(12) United States Patent
Kim

(10) Patent No.: US 9,153,009 B2
(45) Date of Patent: *Oct. 6, 2015

(54) MOTION SICKNESS REDUCTION

(76) Inventor: Samuel Kim, Englewood Cliffs, NJ (US)

( * ) Notice: Subject to any disclaimer, the term of this patent is extended or adjusted under 35 U.S.C. 154(b) by 702 days.

This patent is subject to a terminal disclaimer.

(21) Appl. No.: 12/381,612

(22) Filed: Mar. 13, 2009

(65) Prior Publication Data

US 2009/0179987 A1  Jul. 16, 2009

Related U.S. Application Data

(63) Continuation of application No. PCT/US2007/020068, filed on Sep. 13, 2007, and a continuation-in-part of application No. 11/166,483, filed on Jun. 24, 2005, now Pat. No. 7,722,526.

(60) Provisional application No. 60/844,424, filed on Sep. 13, 2006, provisional application No. 60/851,984, filed on Oct. 16, 2006, provisional application No. 60/588,710, filed on Jul. 16, 2004, provisional application No. 60/630,055, filed on Nov. 22, 2004.

(51) Int. Cl.
| | |
|---|---|
| H04N 7/18 | (2006.01) |
| G06T 3/40 | (2006.01) |
| G06F 3/01 | (2006.01) |
| A61M 21/02 | (2006.01) |
| A61M 21/00 | (2006.01) |
| G09G 5/00 | (2006.01) |

(52) U.S. Cl.
CPC .................. *G06T 3/40* (2013.01); *A61M 21/02* (2013.01); *G06F 3/011* (2013.01); *A61M 2021/005* (2013.01)

(58) Field of Classification Search
CPC .................................. G06T 3/40; G06T 3/011
See application file for complete search history.

(56) References Cited

U.S. PATENT DOCUMENTS

| | | | |
|---|---|---|---|
| 2,334,018 A | 11/1943 | Mayne | |
| 4,929,228 A | 5/1990 | Hendricks | |
| 4,930,435 A | 6/1990 | Newman | |
| 5,067,941 A | 11/1991 | Hendricks | |
| 5,161,196 A | 11/1992 | Ferguson | |
| 5,386,285 A | 1/1995 | Asayama | |
| 5,574,836 A * | 11/1996 | Broemmelsiek | ............. 345/427 |
| 5,647,835 A | 7/1997 | Martineau | |
| 5,966,680 A | 10/1999 | Butnaru | |

(Continued)

OTHER PUBLICATIONS

Michael J. Griffin and Maria M. Newman, "Visual Field Effects on Motion Sickness in Cars", Aviation, Space, and Environmental Medicine, Sep. 2004, vol. 75, No. 9.

(Continued)

*Primary Examiner* — Wen-Tai Lin
(74) *Attorney, Agent, or Firm* — Bergman & Song LLP; Michael Bergman

(57) ABSTRACT

A motion sickness reduction device includes an image capture device for capturing an image device environment and an image display device for displaying image related to the captured image. In order to effectively prevent or reduce motion sickness, the right amount of motion must be displayed on the image display device when the vehicle accelerates or turns. Various methods are disclosed for adjusting the image on the display device and/or the angle of the environment subtended to make the motion sickness reduction device effective.

13 Claims, 35 Drawing Sheets

(56) References Cited

U.S. PATENT DOCUMENTS

| | | | |
|---|---|---|---|
| 6,042,533 A | 3/2000 | Kania | |
| 6,228,021 B1 | 5/2001 | Kania | |
| 6,275,998 B1 | 8/2001 | Tromble | |
| 6,443,913 B1 | 9/2002 | Kania | |
| 6,497,649 B2 | 12/2002 | Parker et al. | |
| 6,663,155 B1 | 12/2003 | Malone et al. | |
| 6,692,428 B1 | 2/2004 | Kania | |
| 6,719,343 B2 | 4/2004 | Emerling et al. | |
| 6,866,225 B2 | 3/2005 | Jones et al. | |
| 6,947,071 B2 | 9/2005 | Eichmann | |
| 7,046,259 B2 * | 5/2006 | Humphries | 345/649 |
| 7,135,961 B1 | 11/2006 | Operowsky et al. | |
| 2001/0000459 A1 | 4/2001 | Kania | |
| 2002/0163215 A1 | 11/2002 | Emerling et al. | |
| 2004/0061793 A1 * | 4/2004 | Fellegara et al. | 348/231.6 |
| 2004/0101165 A1 | 5/2004 | Gallo et al. | |
| 2004/0102676 A1 | 5/2004 | Brendley et al. | |
| 2004/0208394 A1 * | 10/2004 | Kurata | 382/275 |
| 2004/0217234 A1 | 11/2004 | Jones et al. | |
| 2004/0217976 A1 | 11/2004 | Sanford | |
| 2004/0241624 A1 | 12/2004 | Sudo | |
| 2005/0007450 A1 | 1/2005 | Hill et al. | |
| 2005/0167546 A1 | 8/2005 | Jones et al. | |
| 2006/0015000 A1 * | 1/2006 | Kim | 600/27 |
| 2006/0079729 A1 | 4/2006 | Kim | |

OTHER PUBLICATIONS

Patricia M. Burcham, "Motion Sickness Literature Search", Army Research Laboratory, ARL-MR-504, May 2002.

* cited by examiner

MOTION SICKNESS REDUCTION

CROSS-REFERENCE TO RELATED APPLICATIONS

The present application is a continuation of PCT patent application number PCT/US 2007/020068, having an international filing date of Sep. 13, 2007, which claims priority to U.S. provisional patent applications No. 60/844,424, filed on Sep. 13, 2006 and 60/851,984 filed on Oct. 16, 2006, the disclosures of which are herewith incorporated by reference in their entirety, and the benefit of which is herewith claimed. The present application also is a continuation-in-part of co-pending U.S. non-provisional patent application Ser. No. 11/166,483 having a filing date of Jun. 24, 2005 now U.S. Pat. No. 7,722,526, which claims the benefit of U.S. provisional patent application No. 60/588,710 filed on Jul. 16, 2004 and U.S. provisional patent application No. 60/630,055, filed on Nov. 22, 2004.

FIELD OF THE INVENTION

The present invention relates to motion sickness reduction and more particularly to devices and methods for employing visual stimuli to reduce motion sickness.

BACKGROUND

Motion sickness relates to the sense of balance, equilibrium and spatial orientation. The sense of balance is controlled and maintained by an intricate interaction of multiple parts of the human body, specifically, the inner ears (also called the labyrinth), the eyes, skin pressure receptors, muscle and joint sensory receptors, and the central nervous system.

The inner ears monitor motion, such as turning and tilting. The eyes monitor body orientation in space (i.e. upside down, right side up, etc.) and also directions of motion. The skin pressure receptors, such as those in the joints and spine, determine what part of the body is down and touching the ground or other surfaces. The muscle and joint sensory receptors determine which parts of the body are moving. The central nervous system (the brain and spinal cord), processes all of the information from the four other systems to determine the spatial orientation and motion of the body.

People may get motion sickness when their brains receive conflicting messages. Different people have various degrees of tolerance for these conflicting messages.

It is common knowledge that during operation, a vehicle such as an automobile may pitch as well as yaw and roll. These motions can contribute to motion sickness in an occupant. A passenger inside a ship at sea may see around him just four walls that appear to be stationary, but his body will still feel the motion of the ship. These conflicting signals can lead to motion sickness. A greater rocking motion of the ship will increase the disparity between what the passenger feels and what he sees, and so ships in heavy storms often have many passengers suffering from motion sickness.

An effective way for a person to reduce the likelihood of motion sickness is to look at a stationary point of reference. Ship passengers are commonly advised to get out on the deck and look at a fixed object on land or, if the ship is far out at sea, at the horizon. Thus, as the ship rocks, they can see their own motion relative to a fixed point of reference. If this perceived motion matches the motion they feel, the passengers will avoid motion sickness.

Likewise, a passenger in an automobile can reduce the likelihood of motion sickness by looking out a window at stationary points of reference—buildings, trees, signs, et al. Since the natural tendency for passengers is to look forward, passengers riding in the front seat spend a lot of time looking out the windshield, while rear seat passengers spend much of the time looking at the back of the seat in front of them. Because of this, passengers in the rear seat of an automobile are more likely to suffer from motion sickness than front-seat passengers.

The symptoms of motion sickness can include a general feeling of being unwell (malaise), nausea and vomiting, or both, headaches, cold sweating and a pale appearance. Symptoms may alleviate when the motion stops; however, it has been found that for some people it can take a significant period of time for symptoms to subside.

U.S. Pat. No. 6,692,428 to Kania discloses an apparatus having a sensor that detects a motion of an object and a sensory converter which converts the detected motion to corresponding sensory signals, which can be audio, white noise or video. The sensory signals are designed to alleviate motion sickness by using varying audio frequencies and/or colors displayed to the user selected in proportion to the determined motion. In addition, U.S. Pat. No. 6,497,649 to Parker, et al., discloses displaying an independent visual background via a head-mounted display with a visual reference corresponding to the perceptions of a person's vestibular system.

Another attempt to prevent motion sickness is disclosed in U.S. Pat. No. 6,275,998 to Tromble which shows a vision occluding eye shield which completely blocks the peripheral vision of the wearer to the discernment of motion and which blocks most or all of the superior field of vision of the wearer. When worn by a passenger, the device blocks perception of objects passing through the peripheral field of vision in the side windows and through the front window, while allowing the wearer to focus on tasks or objects within the vehicle by looking through the unoccluded portion.

There have also been many attempts to treat motion sickness medically, with pharmaceutical solutions and other medicinal treatments. Some preventative medications can be purchased without a prescription (e.g., Dramamine®, Bonine®, Marezine®). Stronger medicines such as tranquilizers and nervous system depressants usually require a prescription.

The downside of using any of these medications includes cost, inconvenience, and potential side effects.

Other medical solutions involve the use of magnetic or metallic bracelets and/or jewelry. Some jewelry is worn on pressure points in an attempt to alleviate motion sickness. It has been found however, that such devices have limited success in preventing motion sickness. As such there exists a need for an effective apparatus, system and method for preventing motion sickness without using medications or medical devices.

The afore-mentioned problems, drawbacks, and disadvantages, in addition to others, are alleviated by the present invention disclosed herein where an object thereof is to provide a non-intrusive, non-medicinal, safe and effective system, method and apparatus for preventing motion sickness while reading text or viewing an image.

SUMMARY OF THE INVENTION

The inventor has recognized that there is a need for an improved device capable of presenting visual stimuli to an observer in order to reduce a likelihood that the observer will experience motion sickness. The inventor has further recognized that it is advantageous to have a device capable of automatically adjusting to observer activities and environmental conditions in order to improve and/or optimize the effectiveness of the device in reducing the likelihood of motion sickness. Having made the foregoing discoveries and conclusions, the inventor has invented a device and method for reducing motion sickness and a method of adjusting a motion sickness reduction device including, among others, moving an image presentation device in relation to a viewer; and adjusting an image on said image presentation device to reduce a motion sickness response of said viewer.

The following description is provided to enable any person skilled in the art to make and use the disclosed inventions and sets forth the best modes presently contemplated by the inventor of carrying out their inventions. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present inventions.

DETAILED DESCRIPTION

The inventor has discovered that a risk of motion sickness, and the severity of motion sickness experienced, can be reduced by providing visual stimuli to the occupant of a dynamic environment such as a moving vehicle. With this in mind, the inventor has invented the various systems, devices and methods described and claimed in this application. Among these are the described embodiments including a video camera adapted to capture a dynamic image of a surrounding environment and a video display screen coupled to a moving vehicle and positioned for viewing by an occupant of the vehicle. The invention includes methods and apparatus to improve the character and effectiveness of the motion sickness reduction device by adjusting and controlling various aspects of the visual stimuli presented to the occupant.

Figure 1:
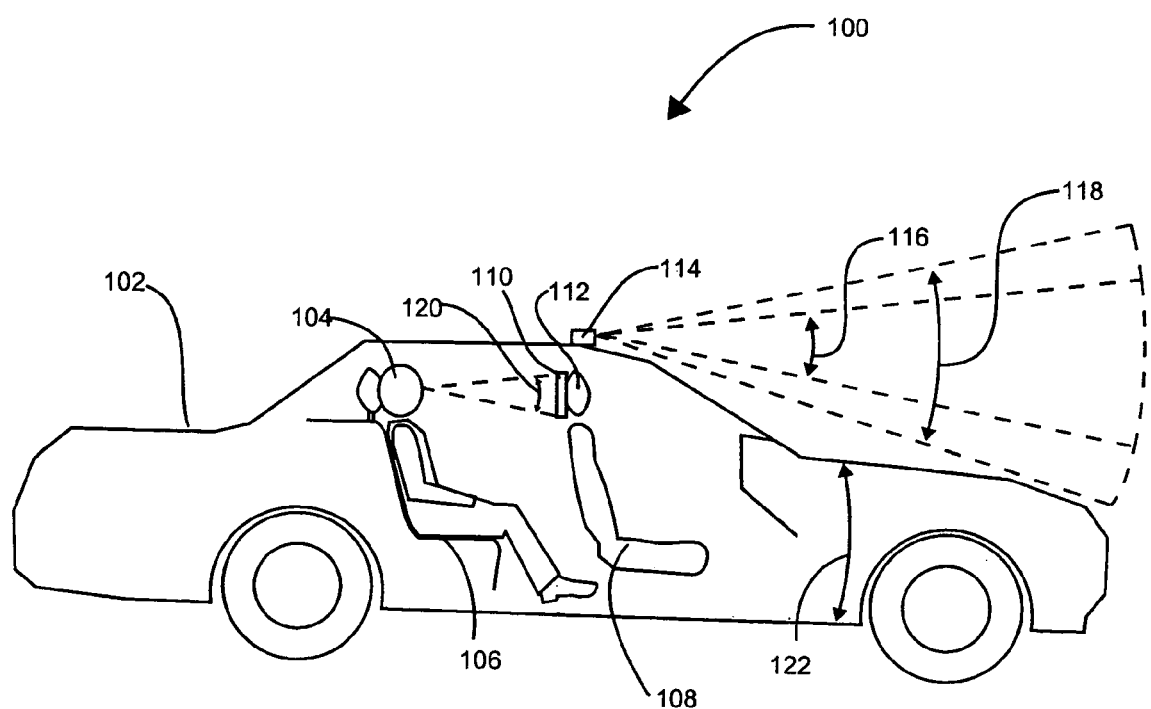
FIG. 1 shows, in side elevation, a vehicle including a motion sickness reduction device according to one embodiment of the invention.

FIG. 1 shows an exemplary vehicle including a motion sickness reduction device 100 according to one embodiment of the invention. In other exemplary embodiments the occupant 104 is seated in a rear seat 106 of the automobile 102. As will be further described below, the present invention is adaptable to a wide variety of arrangements, including arrangements in which the occupant 104 is located in a front seat 108, in standing supports, reclining supports, prone supports, and positioning in which the occupant 104 is relatively remote from a front seat 108.

In the illustrated embodiment, a visual stimulus device such as, for example a video display screen 110 is coupled to a posterior surface 112 of the front seat 108. The video display screen 110 is adapted to present a dynamic image such as a video image for viewing by the occupant 104. An image capture device such as a camera 114 is coupled to the automobile 102. In one embodiment, the camera 114 is substantially fixedly coupled to the automobile 102 so that the camera and automobile move synchronously with respect to a surrounding environment. In the FIG. 1 embodiment, the camera is adapted to capture an image looking forwardly from the automobile 102.

As further illustrated in FIG. 1, a dimension of the video screen 110 and a spatial displacement between an eye of the occupant 104 and the video screen 110 results in a vertical effective viewing angle 120. The vertical effective viewing angle is an effective viewing angle 120 were the viewing angle is disposed in a substantially vertical plane. As will be discussed in additional detail below, effective viewing angles on different axes may differ. The camera 114 has a corresponding vertical effective viewing angle 116. In one embodiment of the invention, the camera 114 includes a zoom lens adapted to provide an adjustable depth of focus and a variable effective viewing angle up to a maximum effective viewing angle 118.

Figure 2:
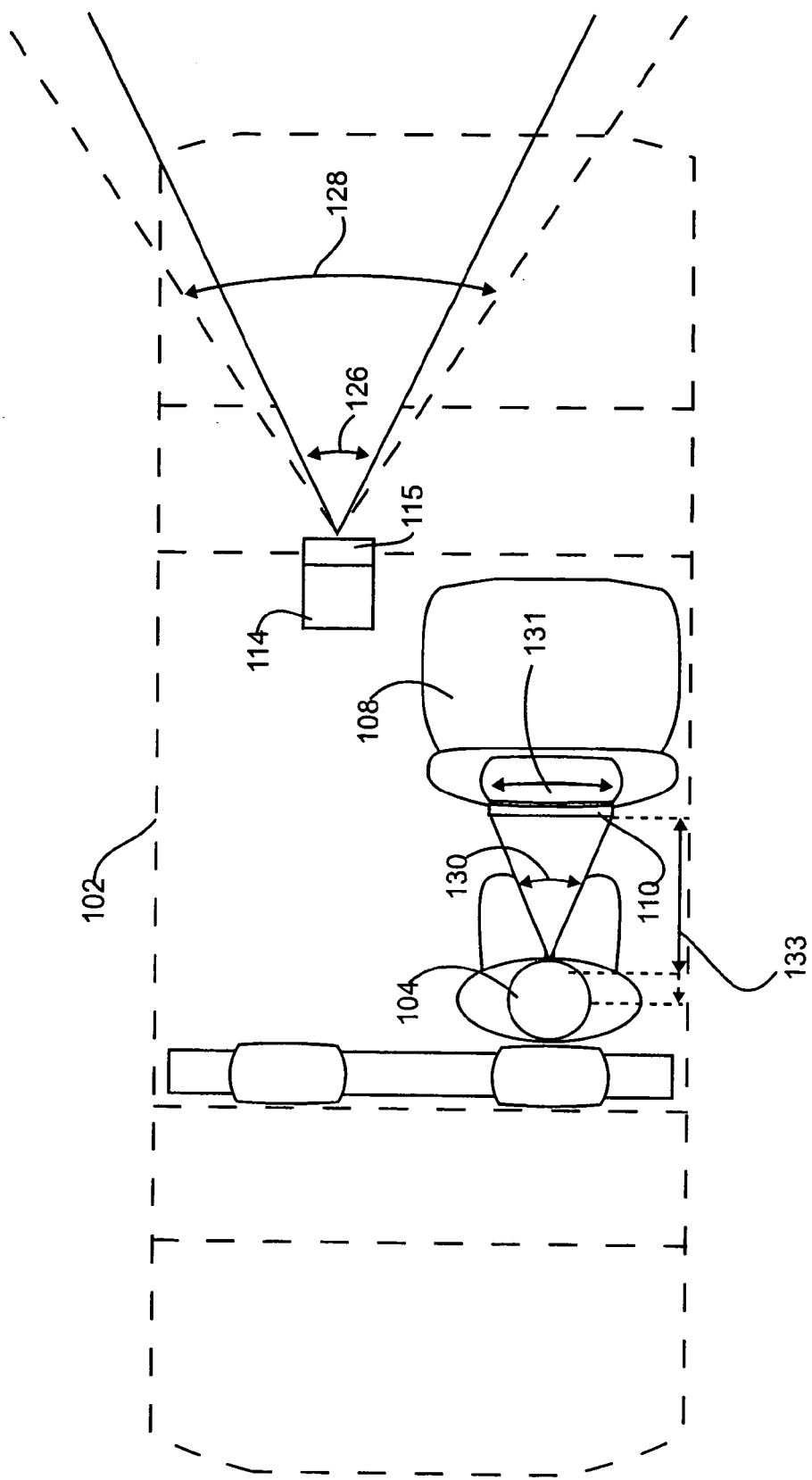
FIG. 2 shows, in schematic top view, a vehicle including a motion sickness reduction device according to another embodiment of the invention.

FIG. 2 shows, in plan view, a further aspect of the invention as illustrated in FIG. 1. In FIG. 2 the occupant 104 is shown disposed within the vehicle 102. Again, the video screen 110 is coupled to the posterior surface of the front seat 108. The video screen 110 has an active area with a horizontal dimension 131. The screen 110 is placed at a distance 133 from the eyes of occupant 104. Consequently, the active area spans a horizontal effective viewing angle 130 of the occupant 104, where the horizontal effective viewing angle is a function of the horizontal dimension 131 and the distance 133.

In the FIG. 2 embodiment, the camera 114 is shown mounted on an upper external surface of the vehicle 102. As shown camera 114 includes a zoom lens 115 that is adapted to control a horizontal effective viewing angle 126 of the camera 114. The horizontal effective viewing angle 126 is adjustable over a range of viewing angles up to a maximum horizontal viewing angle 128.

Figure 3:
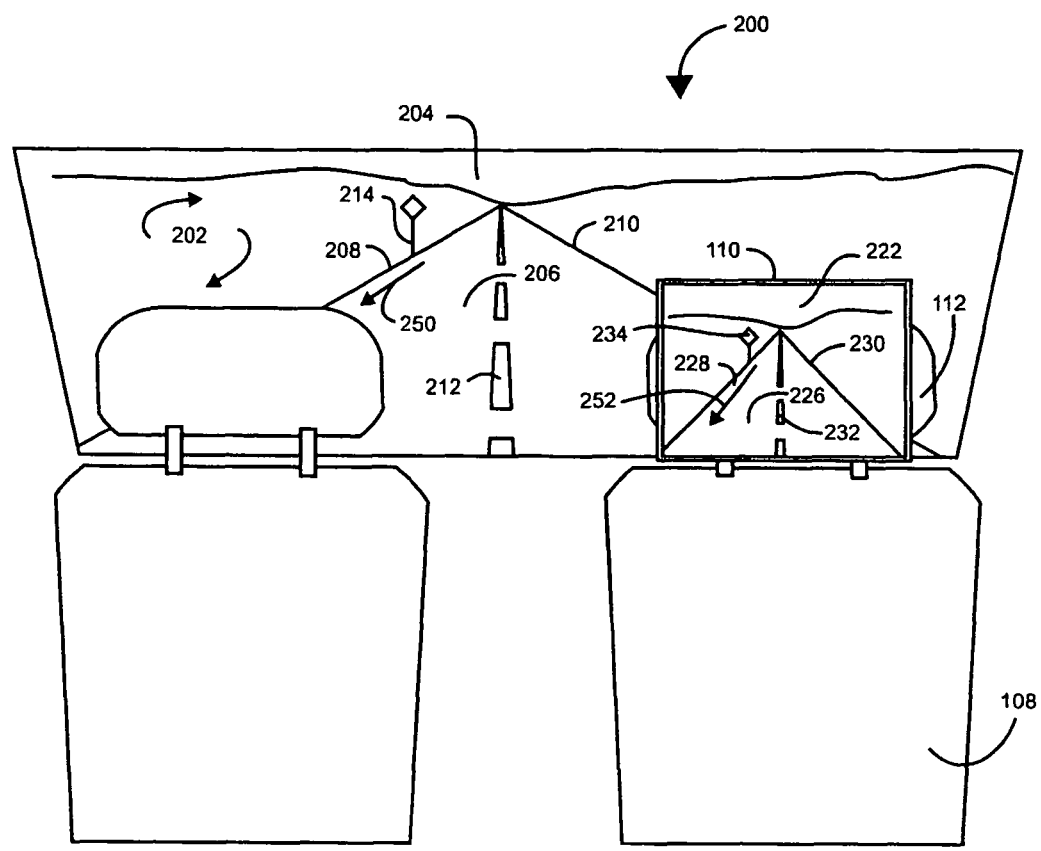
FIG. 3 shows a view outwardly from within a vehicle according to one embodiment of the invention.

FIG. 3 shows a view 200 from within an automobile according to one embodiment. As in FIG. 1, a video screen 110 is coupled to a posterior surface 112 of a front seat 108. The video screen 110 is disposed to allow viewing by a rear seat occupant. For reference, an exemplary external environment 202 is shown as viewed through a windscreen 204. The exemplary external environment includes a landscape having a road 206 with left 208 and right 210 edges and a centerline 212. Correspondingly, the video screen 110 shows a video screen image 222 of the exemplary external environment 202. The image includes a road image 226 of the road 206 with a corresponding left edge image 228, a corresponding right edge image 230, and a centerline image 232. A reference landmark 214 in the exemplary external environment 202 has a corresponding image 234 within the video screen image 222.

During operation of the automobile according to one embodiment of the invention, the automobile moves forward with respect to the exemplary external environment 202. This relative motion between the automobile and its environment is visually perceived by the occupant, both by viewing the environment 202 through the windscreen 204 and by viewing the image of the environment 222 on the video screen 110. One of skill in the art will appreciate that, in various embodiments, no view of the external environment 202 is available to a subject occupant, as where no windscreen 204 exists or where the view of such a windscreen is obscured.

In one aspect, the acceleration of the vehicle 102 relative to the environment 202 causes an apparent motion 250 of the reference landmark 214 downwardly and towards the left of the windscreen 204. A corresponding motion 252 of the image 234 of the reference landmark 214 proceeds downwardly and to the left across the video screen 110. The occupant 104 will perceive the acceleration of the vehicle 102 visually, through motions 250 and 252, and viscerally through corporeal acceleration sensing mechanisms, including the vestibular system of the occupant's inner ear.

Figure 4:
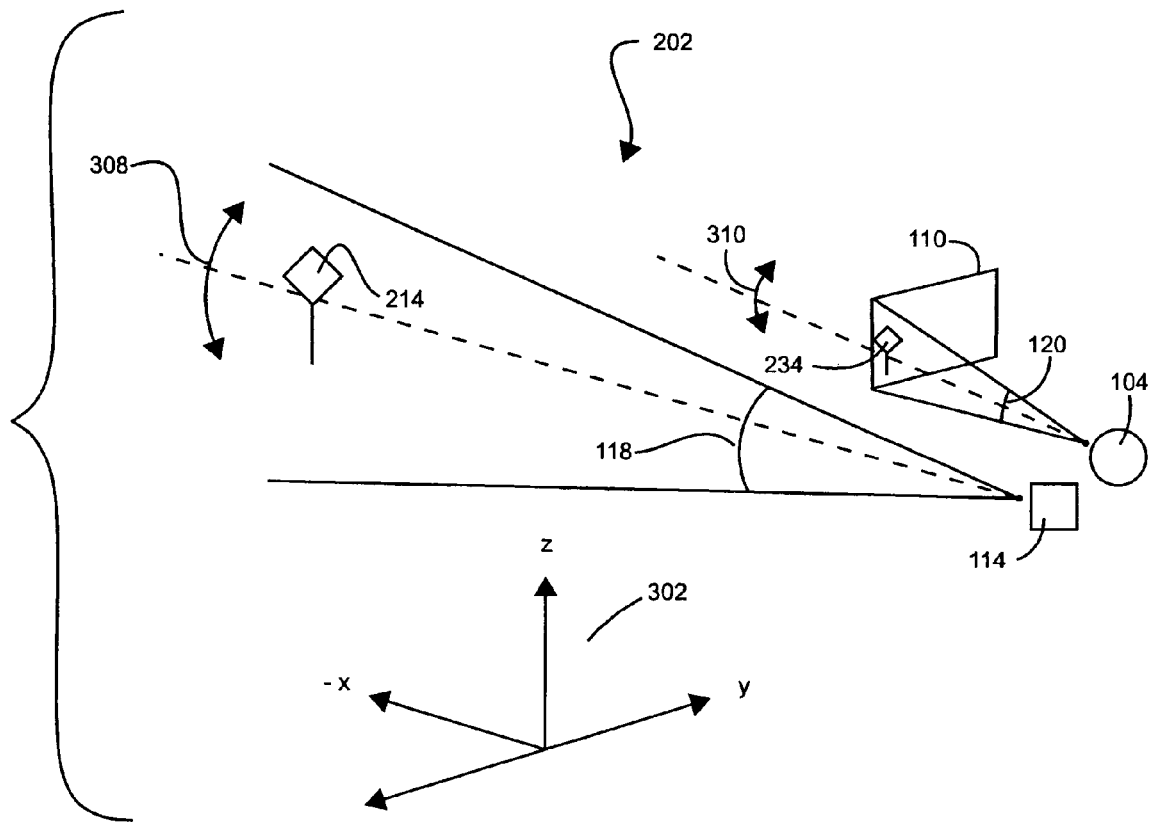
FIG. 4 shows a geometrical schematic diagram illustrating spatial relationships between various system components and environmental elements according to an exemplary embodiment of the invention.

FIG. 4 shows a schematic representation, in perspective view, of an environment 202 as perceived by an occupant of the vehicle such as, for example, the occupant 104 of vehicle 102 of FIG. 1. A set of coordinate axes 302 is provided in FIG. 4 for reference purposes. The coordinate axes 302 identify a negative X direction corresponding to a horizontal direction forwardly away from the occupant 104 (of FIG. 1), and generally an average direction of motion of the automobile 102. The y-axis corresponds to a horizontal direction perpendicular to the x-axis and the z-axis corresponds to a direction substantially vertical with respect to the environment.

Angle 118 is a vertical effective viewing angle of an exemplary camera 114 such as that shown, for example, in FIG. 1. A video screen 110 spans a vertical effective viewing angle 120 of an occupant 104 of an automobile 102. One may assume that, initially, the video screen 110 as a viewing surface disposed substantially parallel to the y-z plane. When the automobile 102 is in motion, it traverses space with a time average motion substantially along the −x direction. However, when operating in a real-world environment, the automobile in motion also will tend to experience roll, yaw, and pitch motions, such as the pitch motion 122 illustrated in FIG. 1. In addition, the automobile will experience linear acceleration in all three dimensions.

Assuming that the occupant 104 of the automobile 102 and the video camera 114 substantially remain in a common reference frame, pitching motion 122 will cause, for example, an apparent angular motion of the external environment 202. This angular motion will appear to be an angular rotation of the external environment including various elements of the environment such as, for example, a relative pitching motion 308 of a reference landmark 214. Assuming that the image on the video screen 110 reflects that detected by the camera 114, a corresponding pitching motion 310 will be evident in the video screen image 234 of the reference landmark.

Again, surprisingly, the inventor has discovered that maintaining a correspondence between the respective angular velocities of pitching motions 308, 310 is effective to reduce the likelihood and/or severity of motion sickness in occupant 104.

Without intending to be bound to a particular theory of operation, it is believed that by maintaining the perceived angular velocity of pitching motion 310 substantially equal to the perceived angular velocity of pitching motion 308 as viewed at the camera 114, the visual image cues perceived from the video screen 110 by the occupant 104 are brought into concordance with the corporeal acceleration sensing mechanisms of the occupant.

Figure 5:
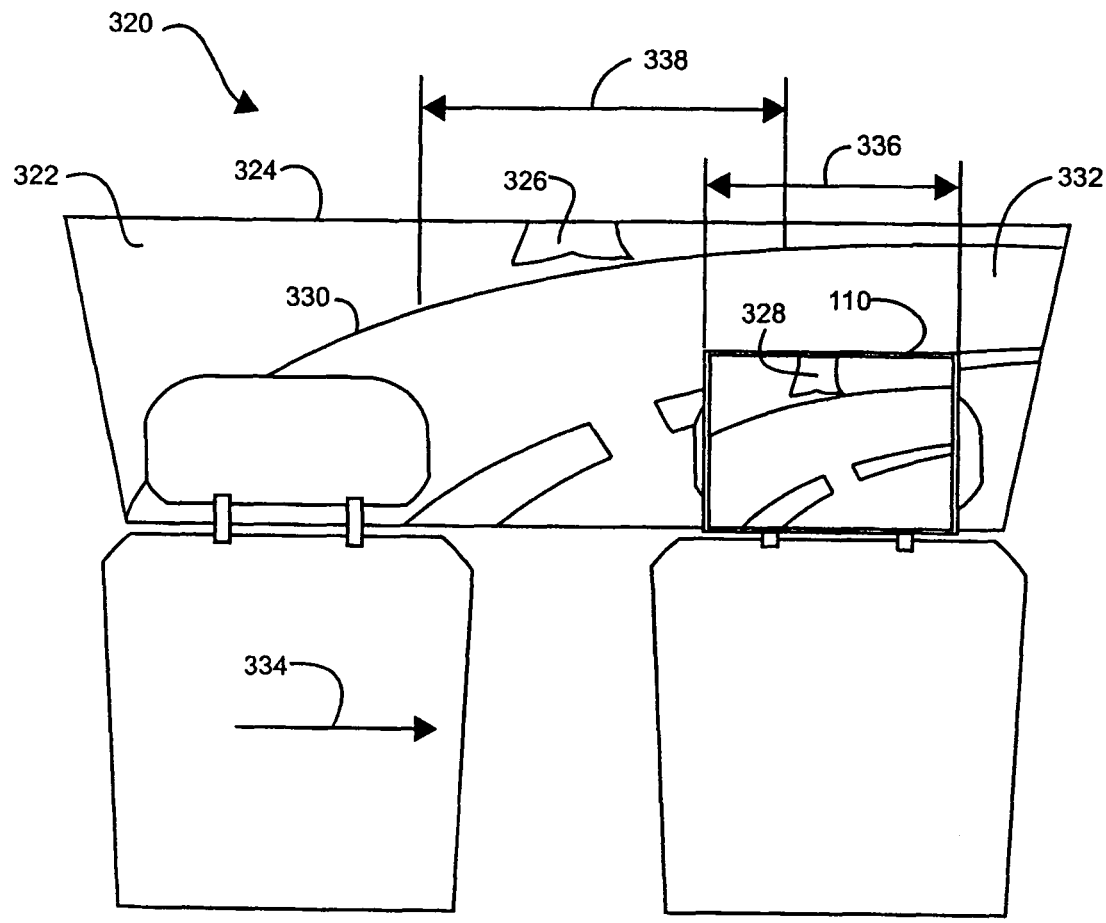
FIG. 5 shows a view outwardly from within a vehicle according to one embodiment of the invention.

FIG. 5 shows an interior view of a vehicle 320 including a motion sickness reduction device according to one embodiment of the invention. The interior view of the vehicle 320 is presented from a perspective of an occupant of a rear seat of the vehicle. The interior view of the vehicle 320 includes a video display screen 110. An external view of an environment 322 as viewed through a windscreen 324 of the vehicle is also visible. The external environment 322 includes a landmark such as a base of a tree 326. An image 328 of the base of the tree is visible on the video display screen 110.

In the exemplary circumstances illustrated, the vehicle is operating to traverse a curve 330 in a road 332. As the vehicle traverses the curve 330, the vehicle as a whole rotates to the right 334. Consequently there is an apparent motion of the base of the tree 326 from right to left across the windscreen 324. There is a corresponding motion of the image 328 of the base of the tree from right to left across the video display screen 110.

According to one embodiment, the invention includes a method for calibrating the motion sickness reduction device so as to have a motion of the image 328 of the base of the tree across the display screen 110 apparently equal in length to a corresponding motion of the base of the tree 326 across the windscreen 324. In other words, during the time interval that it takes for the image 328 of the base of the tree to traverse distance 336 the base of the tree as perceived by the viewer through the windscreen traverses a distance 338 that is equal to the first distance 336.

Figure 6:
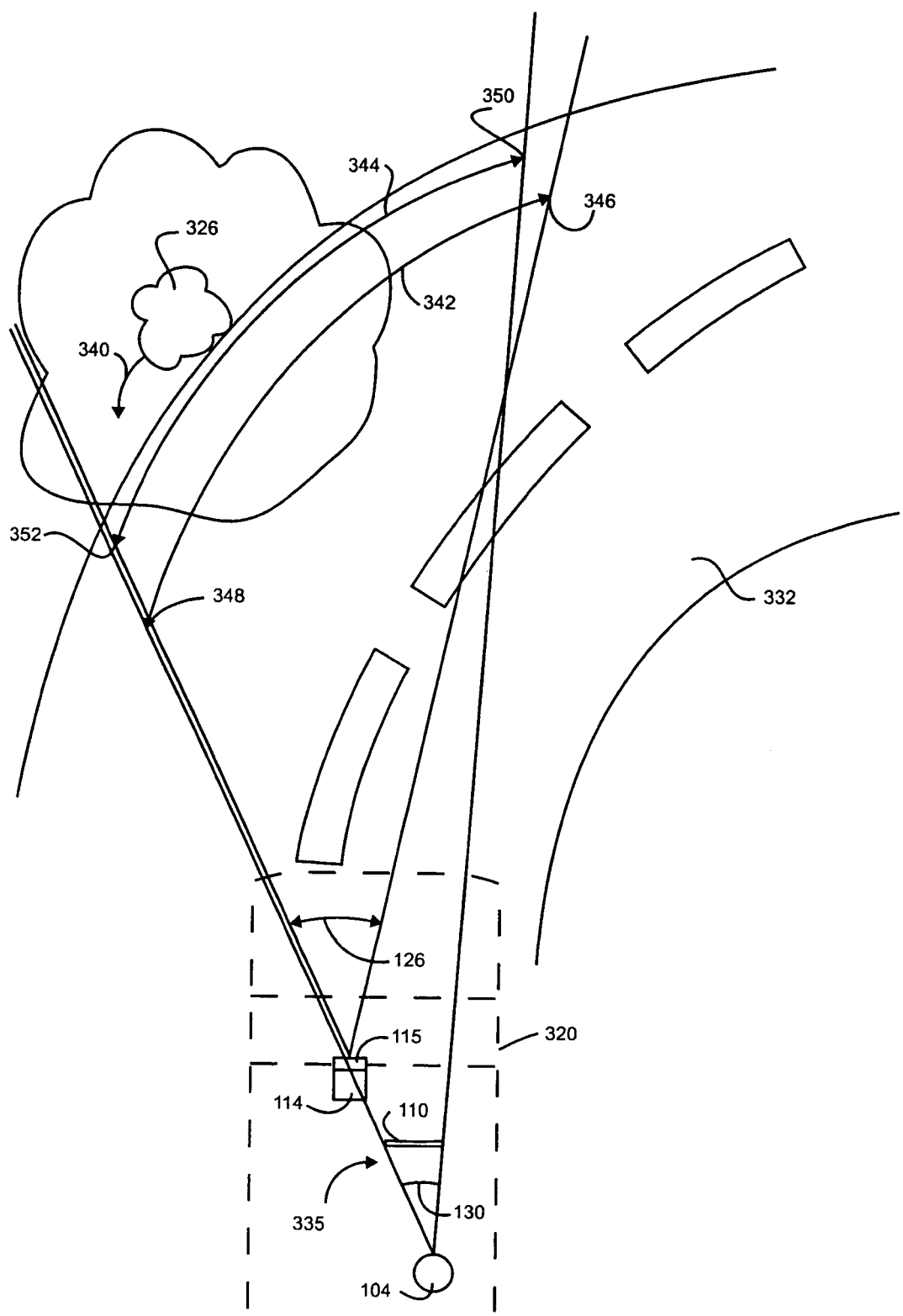
FIG. 6 shows, in schematic plan view form, an environment including a vehicle with a motion sickness reduction device according to one embodiment of the invention.

FIG. 6 shows the vehicle and environment of FIG. 5 in schematic plan view form. As illustrated in FIG. 6, a vehicle 320 is disposed on and progressing forwardly on the road 332. The road is curved so that as the vehicle 320 proceeds, it rotates (yaws) clockwise 335, as viewed from above. From the perspective of a vehicle occupant 104 this clockwise rotation 335 causes an apparent leftward motion (counter-clockwise rotation) 340 of the base of the tree 326.

A video camera 114 includes a zoom lens 115 that is set to a horizontal effective viewing angle 126 so as to provide a first field of view 342. Within the field of view of the occupant 104, the video display screen 110 subtends a horizontal effective viewing angle 130 which, when extrapolated to the plane of the base of the tree 326 provides a second field of view 344.

As illustrated, the zoom of the camera 114 is set to provide a first field of view 342 that is substantially equal to the second field of view 344. Consequently, as the car rotates clockwise 335, the tree traverses the field of view of the camera 342 during substantially the same time interval over which it would traverse a corresponding field of view of the passenger 344, as viewed through the video display screen 110. In other words during a particular time interval, the tree appears to traverse from a rightward edge 346 to a leftward edge 348 of the field of view 342 and concurrently from a rightward edge 350 to a leftward edge 352 of field of view 344.

Figure 7:
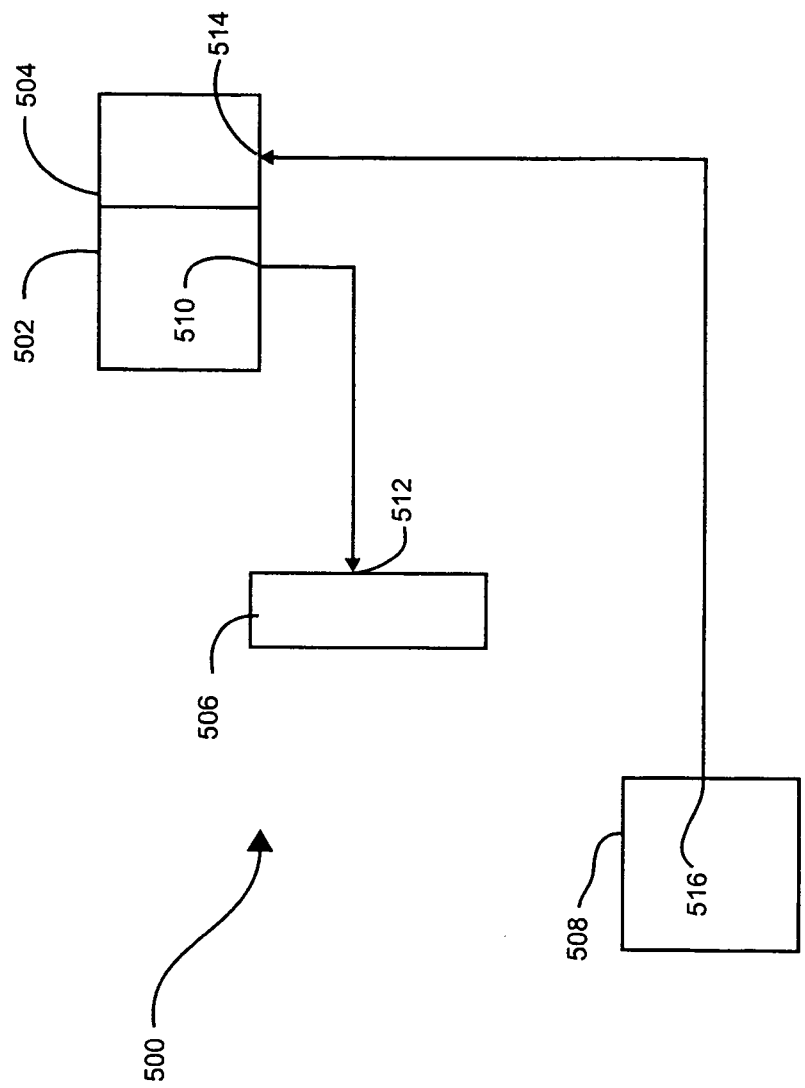
FIG. 7 shows, in block diagram form, a motion sickness reduction device according to one embodiment of the invention.

FIG. 7 shows, in block diagram form, an image sensing system 500 according to one embodiment of the invention. In the illustrated embodiment, the image sensing system 500 includes a video camera 502, a zoom lens device 504, an image display device 506, and a zoom control transducer 508. An image signal output 510 of camera 502 is coupled to an image signal input 512 of display device 506. In the illustrated embodiment, this coupling includes, for example a coaxial cable. One of skill in the art will appreciate, however, that a wide variety of coupling devices and arranges may be employed to convey an image signal from the camera 502 to the display device 506. A control signal input 514 of zoom lens 504 is coupled to a control signal output 516 of zoom control device 508. In the illustrated embodiment, this coupling includes, for example an electrical cable. One of skill in the art will appreciate, however, that a wide variety of coupling devices and arranges may be employed to convey an image signal from the camera 502 to the display device 506, including fiber-optic devices etc.

According to one embodiment, the zoom control device is disposed adjacent to, for example, a hand of a vehicle occupant such as exemplary occupant 104 of FIG. 1. According to one embodiment of the invention, the occupant of the vehicle operates the zoom lens 504 of the camera 502 by remote control using the control input 506 to adjust the zoom level of the zoom lens five of four. In one embodiment of the invention, adjustment of the zoom lens is performed prior to commencing travel in an automobile. In another embodiment of the invention, adjustment of the zoom lens is performed periodically or intermittently during the course of a trip in the automobile.

In one embodiment, the invention includes a method of adjusting the zoom lens 504 of the camera 502 so as to maintain a video image on the display device 506 in a way that keeps the motion of an image across the display device 506 concordant with a physical motion of the automobile. Specifically, in one embodiment of the invention, the zoom 504 is adjusted so that the angular velocity of an external landmark or other feature of the environment across the screen of the display device 506 is equal to a corresponding angular velocity of the landmark or environmental feature with respect to the automobile.

In one embodiment of the invention, an occupant of the automobile turns a knob to adjust a zoom level of the zoom lens 504. In another embodiment of the invention, the occupant of the vehicle manipulates a joystick to adjust the zoom level of the zoom lens 504. In another embodiment of the invention, and occupant depresses one or more pushbuttons to adjust the zoom level of the zoom lens 504. In still another embodiment of the invention, the occupant of the vehicle manipulates a mouse in relation to a graphical icon displayed on the display device 506 to adjust a zoom level of the zoom lens 504, and in yet another embodiment of the invention, an occupant of the vehicle issues a voice command to adjust a zoom level of the zoom lens 504.

It should be noted that the motion sickness reduction device 500 of FIG. 7 includes direct coupling between, for example, the video camera 502 and the display device 506. In another embodiment of the invention, an address driven bus architecture is used in place of direct signal connection. Such an address driven bus architecture is illustrated, for example, in FIG. 8.

Figure 8:
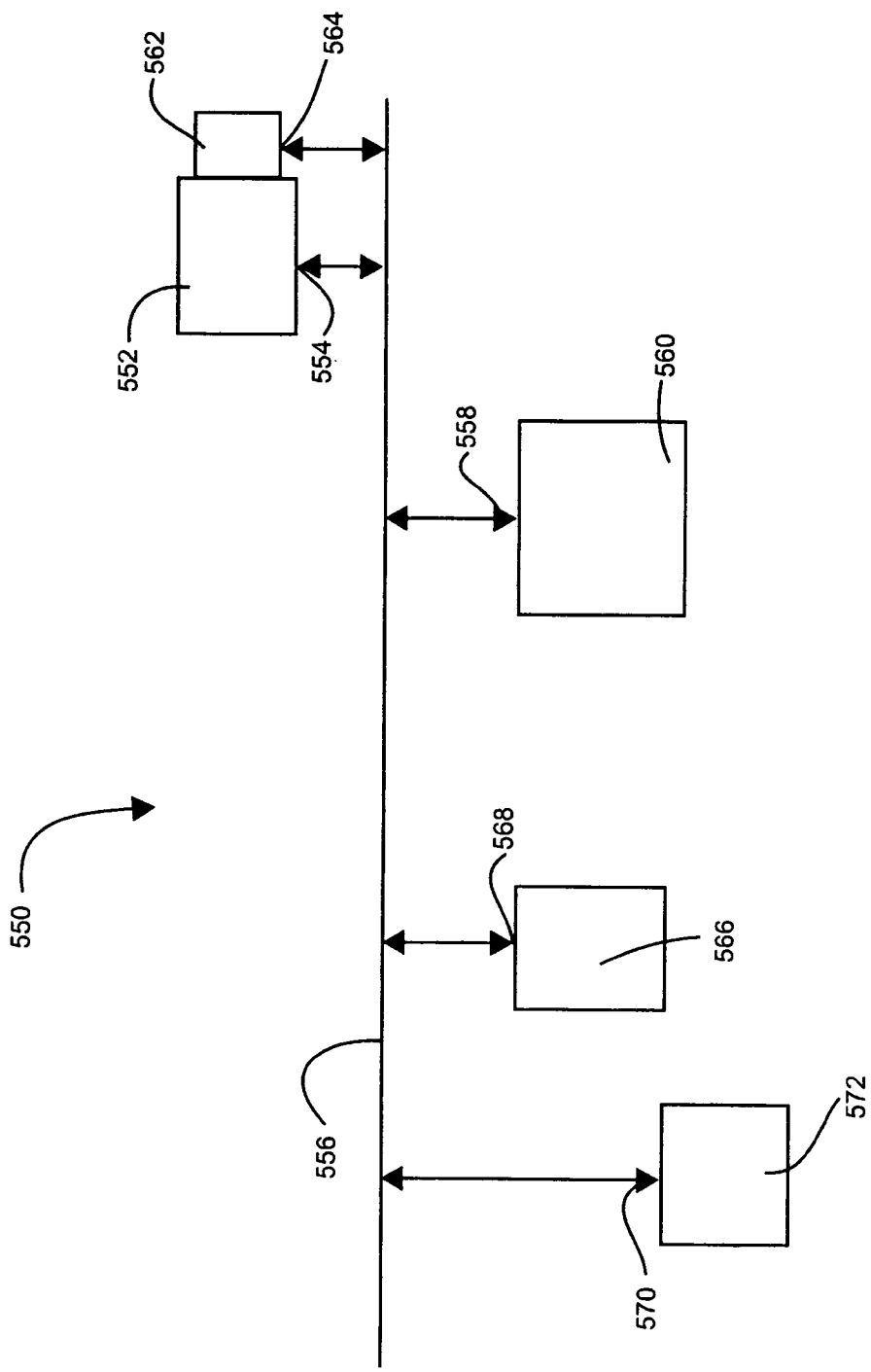
FIG. 8 shows, in block diagram form, a motion sickness reduction device according to another embodiment of the invention.

FIG. 8 shows, in block diagram form, motion sickness reduction system 550 according to one embodiment of the invention. In the illustrated embodiment, the motion sickness reduction system 550 includes a video camera 552 with a communications port 554. The communication port 554 is coupled to a communication bus 556. As would be understood by one of ordinary skill in the art, the communication bus 556 is an address driven communication bus.

In various embodiments of the invention, the communication bus 556 includes a tangible communication medium such as an electronic wire, a coaxial cable, a waveguide and an optical fiber, for example. In other embodiments, a communication function of the communication bus is provided by a wireless communication system such as, for example, a radio frequency wireless communication system and/or an optical frequency wireless communication system. Also in various embodiments the communication bus 556 includes a bus for parallel data communication. In one embodiment of the invention, the parallel data communication bus includes one or more data lines, a plurality of address lines and one or more control lines. In another embodiment of the invention, the communication bus 556 includes a bus for serial data communication. According to one embodiment of invention, the serial data communication bus is adapted to convey a digital data packet including an address data portion and a payload data portion.

The communication bus 556 is coupled to a communication port 558 of a processor device 560. According to various embodiments of the invention, the processor device 560 is a microprocessor device such as a microcontroller device. In one embodiment of the invention, the processor device 560 is adapted to receive image data related to an image received by the video camera 552 and produce a processed image data corresponding to a processed image. In a further aspect of the invention, the processor device 560 is adapted to control the camera 552 by way of control signals received by the camera 552 over the communication bus 556.

In one embodiment of the invention, the video camera 552 includes a zoom lens 562. The zoom lens 562 is adapted to have an adjustable depth of focus and effective viewing angle. According to one embodiment of the invention, the zoom lens 562 is a powered zoom lens including, for example, an electrical transducer such as a motor. The transducer is adapted to adjust a zoom configuration of the zoom lens in response to a control signal. In one embodiment of the invention, the zoom lens includes a lens communication port 564. In one embodiment of the invention, the lens communication port 564 is adapted to be coupled to the communication bus 556 and in one aspect of the invention, the zoom lens 552 is adapted to be controlled by the processor device 560.

The motion sickness reduction device 550 further includes an image display device 566 such as, for example, a video display screen. The image display device 566 also includes a communication port 568 that is adapted to be coupled to the communication bus 556. In a further aspect of the invention, the communication bus 556 is also coupled to a communications input 570 of a user interface device 572.

In operation, the camera 552 is adapted to receive an optical image through the zoom lens device 562. Responsively, the camera 552 produces a image data signal. The image data signal is transmitted from the camera and received over the bus 556 at the processor 560. In various embodiment of the invention, the processor device 560 is adapted to modify the data in the image data signal by, for example, preparing a modified image data signal corresponding to a cropped image. The processor device 560 is adapted to transmit the modified image data signal which is, in turn, received by the display device 566. The display device 566 produces a visual image on the screen thereof in accordance with the invention. The visual image includes, for example, an image corresponding to a portion of the optical image as received by the camera 552. In addition, the visual image may include textual and graphical information that may or may not be related to operation of the motion sickness reduction system 550.

According to one aspect of the invention, the operator interface device 572 is disposed in proximity to an occupant of the vehicle. In operation, the occupant of the vehicle can manipulate the operator interface device 572 to adjust a characteristic of, for example, the visual image on the screen of the display device 566. For example, in one embodiment of the invention, a manipulation of the user interface device 572 causes a control signal to be dispatched from the communication port 570 to the processor device 560.

Responsive to this control signal, the processor device adjusts a characteristic of the modified image data signal. For example, in response to the control signal, the processor may adjust the modified image data signal to produce additional cropping of the visual image produced on the screen of the display device 566.

In one embodiment of the invention, the occupant of the vehicle performs a device calibration activity prior to beginning a trip in the vehicle. During an exemplary calibration activity, the occupant looks in alternating fashion at a video image displayed on the display device 566 and at a view of an external environment, as seen through, for example, a windscreen of the vehicle during a motion of the vehicle. Also during the motion of the vehicle, the occupant adjusts the zoom of the zoom lens 562, or the cropping of an image, as displayed on the display device 566 until an apparent speed of the vehicle in its environment as viewed through the windscreen is substantially equal to an apparent speed of the vehicle in its environment as viewed on the display device 566. According to one aspect of the invention, the angular velocity of a landmark across the windscreen is compared to an angular velocity of a corresponding landmark image across a screen of the display device 566.

In one embodiment of the invention, particular motions of the vehicle are induced so as to facilitate calibration of the motion sickness reduction device. For example, in one embodiment of the invention, the above-described calibration is performed well the subject vehicle performs a turn such as, a leftward turn and/or a rightward turn. In a further embodiment the invention includes the method of performing the above-described calibration while the vehicle traverses a localized variation in elevation; i.e., a bump. In another embodiment of the invention, the vehicle traverses an incline. Still further embodiment of the invention including a method of rotating the vehicle of a horizontal axis and about a vertical axis. In another embodiment, a portion of the vehicle such as, for example a front wheel, is raised and lowered. In yet another embodiment of the invention, the above-described calibration is performed while an external object is moved in relation to the vehicle while the vehicle is moving, or while the vehicle is stationary.

Accordingly in one embodiment of the invention, the vehicle is disposed in a calibration environment where moving elements within the environment are available to provide reference points for performance of the calibration method of the invention. According to one embodiment of the invention, the calibration environment includes a plurality of moving elements especially positioned and operated for calibration of the motion sickness reduction device according to the invention.

According to one embodiment of the invention, calibration of the motion sickness reduction device includes a method of adjusting a zoom of the camera. According to another embodiment of the invention calibration of the motion sickness reduction device includes a method of cropping of a video image. In still another embodiment of the invention, calibration of the motion sickness reduction device includes a method of adjusting a position of a camera with respect to a vehicle to which the camera is coupled. In still another embodiment, the invention includes a method of adjusting a position of a monitor in relation to the vehicle to which the monitor is coupled. Yet another embodiment of the invention includes adjusting a position of a passenger seat in relation to, for example, the vehicle as a whole, location of another passenger seat, the location of a display device, a location and/or attitude of an occupant of the passenger seat, and a motion of the vehicle. Still another embodiment of the invention includes adjusting a position of the occupant had, as for example, by coupling the end of the occupant to an actuator or to a passive restraint that is, in turn, coupled to the passenger seat.

Figure 9:
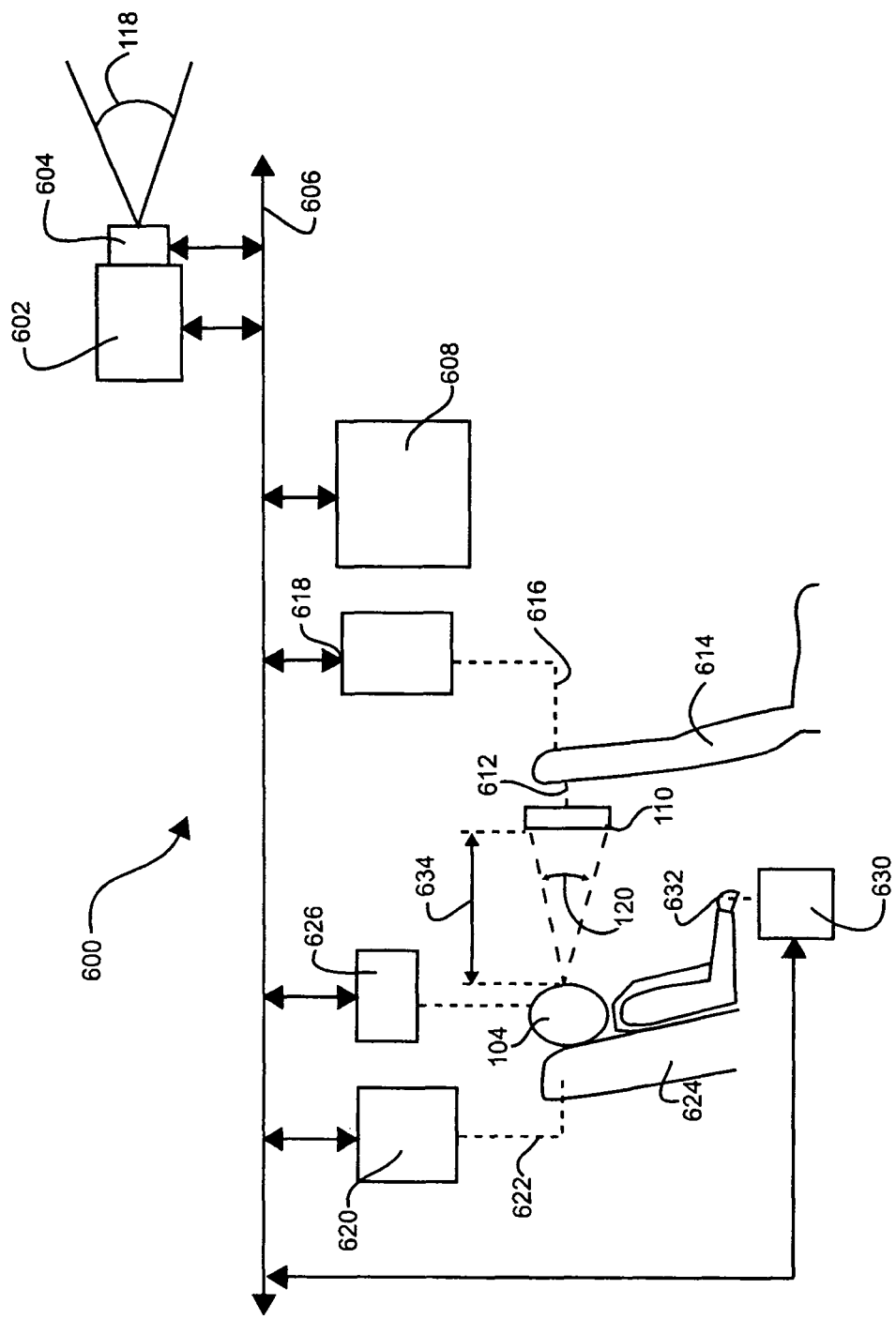
FIG. 9 shows, in block diagram form, a motion sickness reduction device according to still another embodiment of the invention.

As will be described additional detail, various embodiments of the motion sickness reduction device are adapted to be self calibrating; that is to automatically recalibrate or otherwise adjust calibration in response to detect it changes in system characteristics. For example, FIG. 9 shows a motion sickness reduction device 600 according to a one such embodiment of the invention. The motion sickness reduction device 600 includes a video camera 602 having a zoom lens device 604. As in motion sickness reduction device 550 (of FIG. 7), the video camera 602 and the zoom lens device 604 are mutually coupled to a communication bus 606. Also coupled to the communication bus are a processor device 608 and an image display device 110. The image display device 110 is mechanically coupled 612 to, for example, a first passenger seat 614. Also mechanically coupled 616 to the first passenger seat 614 is a first position transducer 618. A second position transducer 620 is mechanically coupled 622 to a second passenger seat 624. The first 618 and second 620 position transducers are mutually coupled to the communication bus 606.

In one embodiment of the invention a third position transducer 626 is adapted to sense a position of a head and/or an eye of an occupant 104 of a vehicle. According to one embodiment of the invention, a human interface device 630 is positioned in proximity to, for example, a hand 632 or a foot of the occupant 104. The third position transducer 626 and the human interface device 630 are both, according to one embodiment of the invention, coupled to the communication bus 606.

Figure 10:
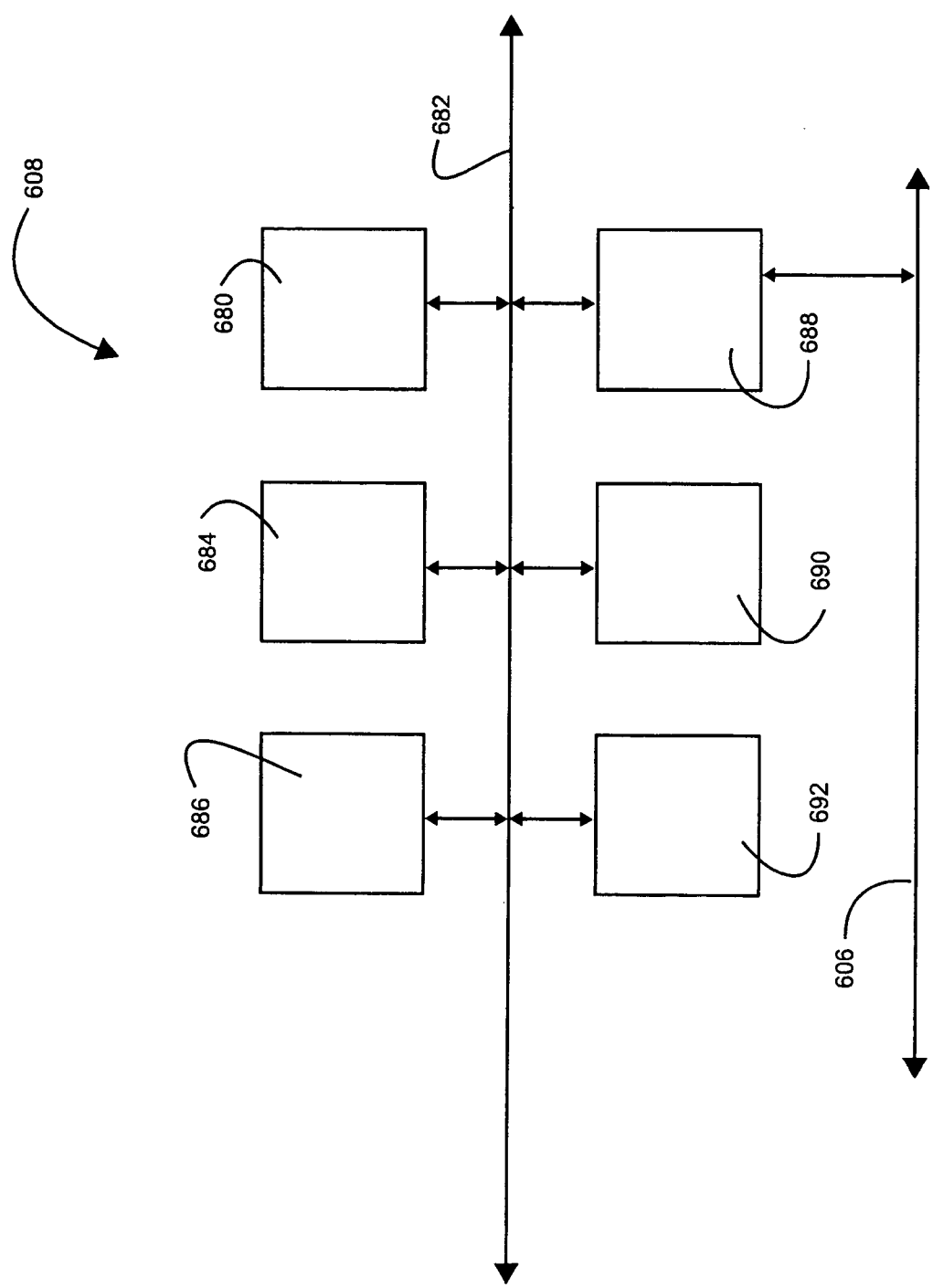
FIG. 10 shows, in block diagram form, a processor device for a motion sickness reduction device according to one embodiment of the invention.

FIG. 10 shows, in additional detail, an exemplary processor device 608 like that illustrated in FIG. 9. According to one embodiment of the invention, the processor device 608 includes a central processing unit 680 coupled to a processor bus 682. In an exemplary embodiment, the processor bus is coupled to a volatile memory device 684 and to a non-volatile memory device 686. One of skill in the art will appreciate that the volatile memory device 684 and nonvolatile memory device 686 may be implemented using any of a wide variety of technologies. For example, the volatile memory device may be a volatile RAM memory device such as a single data rate RAM memory or a double data rate RAM memory. The nonvolatile memory device is, in various embodiments, a read-only memory (ROM), a programmable read-only memory (PROM) an electrically programmable read-only memory (EPROM), and electrically erasable programmable read-only memory (EEPROM), a flash memory, and a magnetic random-access memory (MRAM). The processor bus is also coupled to an I/O interface device 688, which is in turn coupled to, for example, the communication bus 606 of FIG. 9. In additional embodiments, the processor device 608 includes further memory devices such as, for example, a hard disk drive 690 and an optical disc drive 692. As illustrated, the hard disk drive 690 and the optical disk drive 692 are each coupled to the processor bus 682.

Referring now to FIGS. 4 and 9 the operation of the motion sickness reduction device 600 of FIG. 9 will be described according to several exemplary embodiments. As discussed above, the inventor has discovered that, in one embodiment of the invention, it is desirable to have an effective viewing angle 118 of the video camera 602 substantially equal to an effective viewing angle 120 of a vehicle occupant 104. According to one embodiment of the invention, a calibration activity is conducted in order to establish the desired equivalence of viewing angles. The calibration activity is effective to set the effective viewing angle 118 substantially equal to the effective viewing angle 120.

According to one embodiment of the invention, an effective viewing angle 120, subtended by the display device 110, is a function of a linear dimension of an image screen portion of the display device 110, and a distance 634 between the display device 110 and the occupant 104 viewing the display device. Accordingly, it is possible to calculate, or otherwise ascertain, the effective viewing angle 120 under various conditions and circumstances.

According to one embodiment of the invention, this calibration activity is conducted during an initial startup phase of the motion sickness reduction device 600. In another embodiment of the invention, the calibration activity is conducted repeatedly during an operation time interval of the motion sickness reduction device 600. According to one embodiment of the invention the calibration activity includes an analytical calculation adapted to set the effective viewing angle 118 substantially equal to the effective viewing angle 120. In another embodiment of the invention, the calibration activity includes an empirical determination of effective viewing angle by comparison of angular velocities perceived by, for example, the operator 104.

In various embodiments, the illustrated motion sickness reduction device 600 operates to adjust an image viewed by the occupant 104. According to one aspect of the invention, the motion sickness reduction device 600 is adapted to set and/or maintain an effective viewing angle 118 of the camera and lens combination 602, 604 that is substantially equal to an effective viewing angle 120 subtended by the display device 110 as viewed by the occupant 104.

As will be discussed below in additional detail, in one embodiment of the invention, a desired effective viewing angle is set by adjusting a configuration of a zoom lens. In another embodiment of the invention, an effective viewing angle is set by adjusting a size of an image on a display screen, as by cropping, stretching, or shrinking the image. According to one embodiment of the invention, a desired effective viewing angle is calculated by measuring a position of a viewer in relation to a position of a display screen. According to one embodiment of the invention, the position of the viewer is estimated based on a position of an occupant's seat. According to one embodiment of the invention, a position of and occupant's seat is measured using information from a first position transducer. According to another and one of the invention position of a display screen is measured using information from a further position transducer. According to still another embodiment of the invention, a position of the view is directly measured using a further transducer directly coupled to the viewer and/or a further transducer adapted for remote position sensing.

In one embodiment of the invention, the processor 608 receives a standard distance 634 between the occupant 104 and the display device 110. According to one embodiment, this standard distance 634 corresponds to an unadjusted distance between the first passenger seat 614 and the second passenger seat 624. In one embodiment, this standard distance is received at the processor 608 during a configuration operation of the device 600. In another embodiment, the standard distance is received at the processor 608 during manufacture of the vehicle and/or installation of the motion sickness reduction device 600. According to one embodiment of the invention, the standard distance 634 is encoded in the non-volatile memory 686 (as shown in FIG. 10) of the processor device 608.

According to one embodiment of the invention, the processor receives a standard width dimension which is, for example, stored in the nonvolatile memory device 686. This standard width dimension corresponds to a width of the display device 110. In a still further embodiment, the processor receives a standard height dimension, also stored in the nonvolatile memory device 686. This standard height dimension corresponds to a height of the display device 110. As with standard distance 634, the standard width dimension and standard height dimension are received during, for example a configuration operation and/or during installation of the motion sickness reduction device 600. According to one embodiment of the invention, the standard width dimension and standard height dimension are received by the processor device 608 directly from the display device 110 according to a plug and play communication such as is known in the art.

Under the control of the software program stored in the volatile memory device 684 and/or the nonvolatile memory device 686, the processor device 608 identifies a standard effective viewing angle. According to one embodiment, the standard effective viewing angle is readily calculated according to the formula:

Effective viewing angle 120=2×(arc tangent ((½ standard height)/(standard distance 634)) where standard height is a vertical dimension of the viewable image screen portion of the display device 110.

According to another embodiment of the invention, a standard effective viewing angle is available to the central processor unit 680 (as shown in FIG. 10) as a value in a data lookup table. For example, an exemplary data lookup table is stored in the non-volatile memory 686 according to one embodiment of the invention. The data lookup table includes a plurality of data pairs. Each data pair includes a first data value corresponding to a specific distance between a vehicle occupant 104 and a display device 110. Each data pair includes a second data value corresponding to an effective viewing angle 120 correlated to the specific distance. One of skill in the art will appreciate that a plurality of lookup tables including a vertical effective viewing angle lookup table and a horizontal effective viewing angle lookup table are to be employed in various embodiments of the invention. One of skill in the art will also appreciate that a variety of encoding schemes and interpolation schemes, such as are known in the art, are to be used in the preparation and operation of the data lookup tables.

According to one embodiment, the invention includes a method of adjusting the effective viewing angle 118 of the zoom lens 604 so as to match the effective viewing angle 120 subtended by the image display device 110 in relation to the occupant 104. In another embodiment, the invention includes a method of adjusting the image presented on the image presentation device 110 by, for example, cropping, expanding or shrinking the presented image. One of skill in the art will appreciate that image cropping is readily accomplished by selecting and presenting a subset of available image data. Expanding and shrinking of a presented image is accomplished by interpolation of pixel values according to mathematical operations known to those of skill in the art. According to one embodiment of the invention, The requisite cropping, expanding or shrinking of the presented image is accomplished by operation of the processor device 608.

In a further aspect of the invention, an adjusted effective viewing angle is available to the controller device 608 as a calculated value or as a lookup table value, or as a combination of a calculated value and a lookup table value. For example, in one embodiment of the invention, a datum position of the first seat 614 in relation to the second seat 624 is known during initial programming step of the motion sickness reduction device 600.

According to one embodiment, transducer 618 is adapted to detect a differential position of the first seat 614 relative to the datum position of the first seat 614. The transducer 618 transmits a differential position data of the seat 614 to the controller device 608. The controller device 608 receives the differential position data and, under the control of the software program, identifies a target vertical effective viewing angle 120. In various embodiments, identifying the target vertical effective viewing angle 120 includes employing a lookup table, a calculation, or a combination of a lookup table and a calculation. Thereafter, the processor device 608 transmits a control signal, including information related to the identified target vertical effective viewing angle 120, over the communication bus 606 to the zoom lens device 604. The zoom lens 604 receives the control signal and responsibly adjusts a lens arrangement within the zoom lens to provide a vertical effective 118 that is substantially equal to the identified target vertical effective viewing angle 120.

In one embodiment of the invention, Position transducer device 618 provides a first signal to processor device 608 in relation to a position of display screen 110. Position transducer device 620 provides a second signal to processor device 608 in relation to a position of seat 624. Responsively, processor device 608 calculates, or otherwise ascertains, an estimated distance 634 between display screen 110 and eyes of occupant 104. Using this distance, and a known size of display screen 110, processor device 608 ascertains an effective viewing angle 120. In one embodiment of the invention, processor 608 thereafter sends a signal to zoom lens device 604 so as to control an adjustment of effective viewing angle 118. According to one embodiment of the invention, this adjustment of viewing angle 118 serves to set viewing angle 118 substantially equal to viewing angle 120.

According to one embodiment of the invention, occupant 104 provides additional input to processor device 608 by way of human interface device 630. According to such an exemplary embodiment, the input from human interface device 630 allows the processor device 608 to adjust the relationship between effective viewing angles 118 and 120 according to the particular preferences and/or circumstances and environment of an individual occupant 104.

Figure 11:
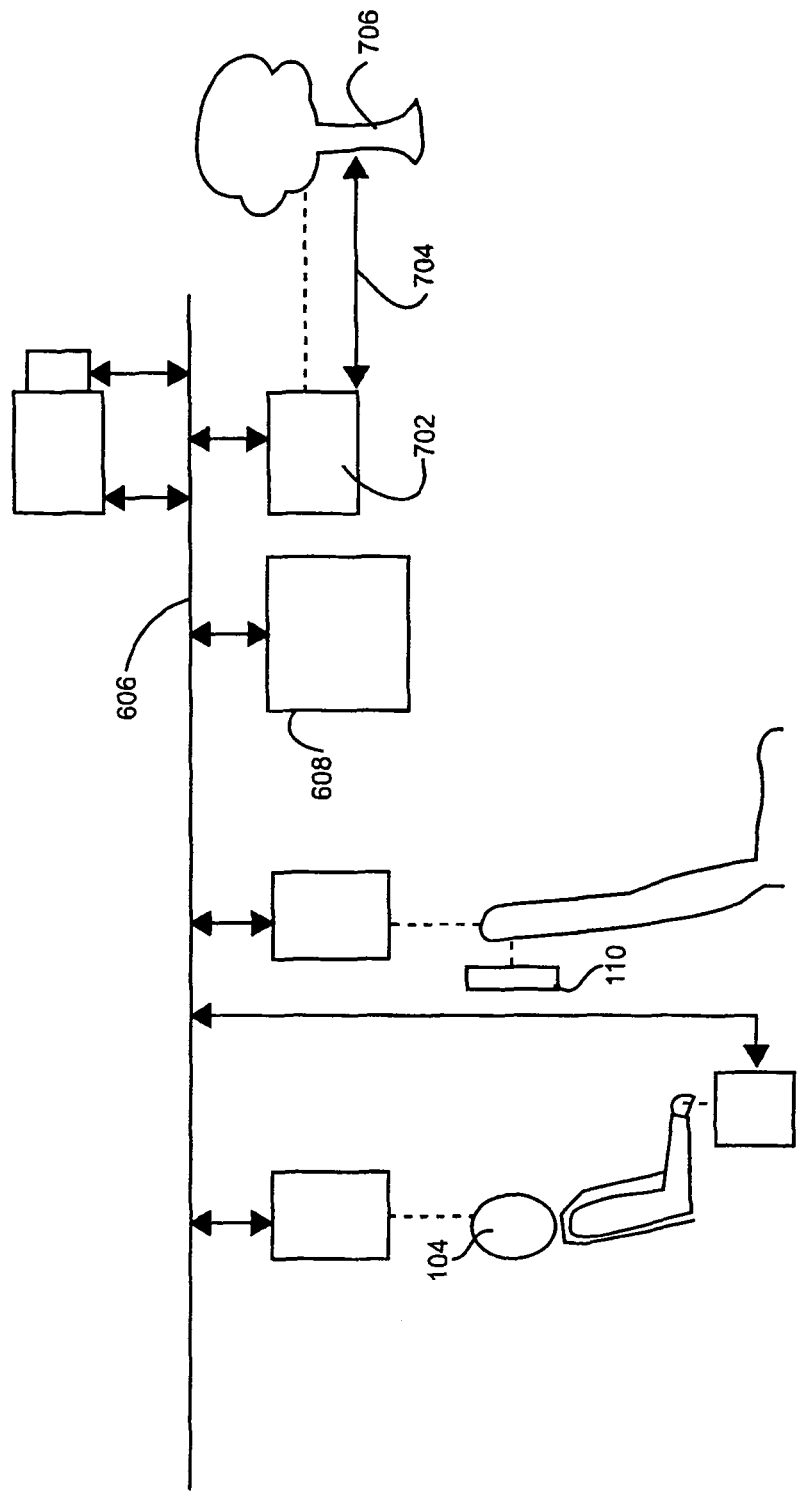
FIG. 11 shows, in block diagram form, a motion sickness reduction device including a rangefinder device according to one embodiment of the invention.

FIG. 11 shows, in block diagram form, a further embodiment of the invention. Like the embodiment of FIG. 9, the FIG. 11 embodiment includes a communication bus 606 and a processor device 608. The FIG. 11 embodiment also includes a rangefinder device 702. The rangefinder device 702 is adapted to ascertain a distance of 704 between the rangefinder device 702 and a landmark in an environment such as, for example a tree 706. According to one embodiment of the invention, a value corresponding to the distant 704 is conveyed from the rangefinder device 702 to the processor device 608. The processor device 608 employs the value transmitted from the rangefinder device 702 to further adjust an effective viewing angle, and/or an image size, according to previously described principles of the invention.

In one embodiment of the invention, a value corresponding to distance 704 is displayed on a display device 110 for viewing by an occupant 104. In another embodiment the rangefinder device 702 is adapted to automatically identify, and range upon, a prominent environmental feature such as a large landmark, a nearby landmark, a visually prominent landmark, approximate vehicle, or other preferred object.

Figure 12:
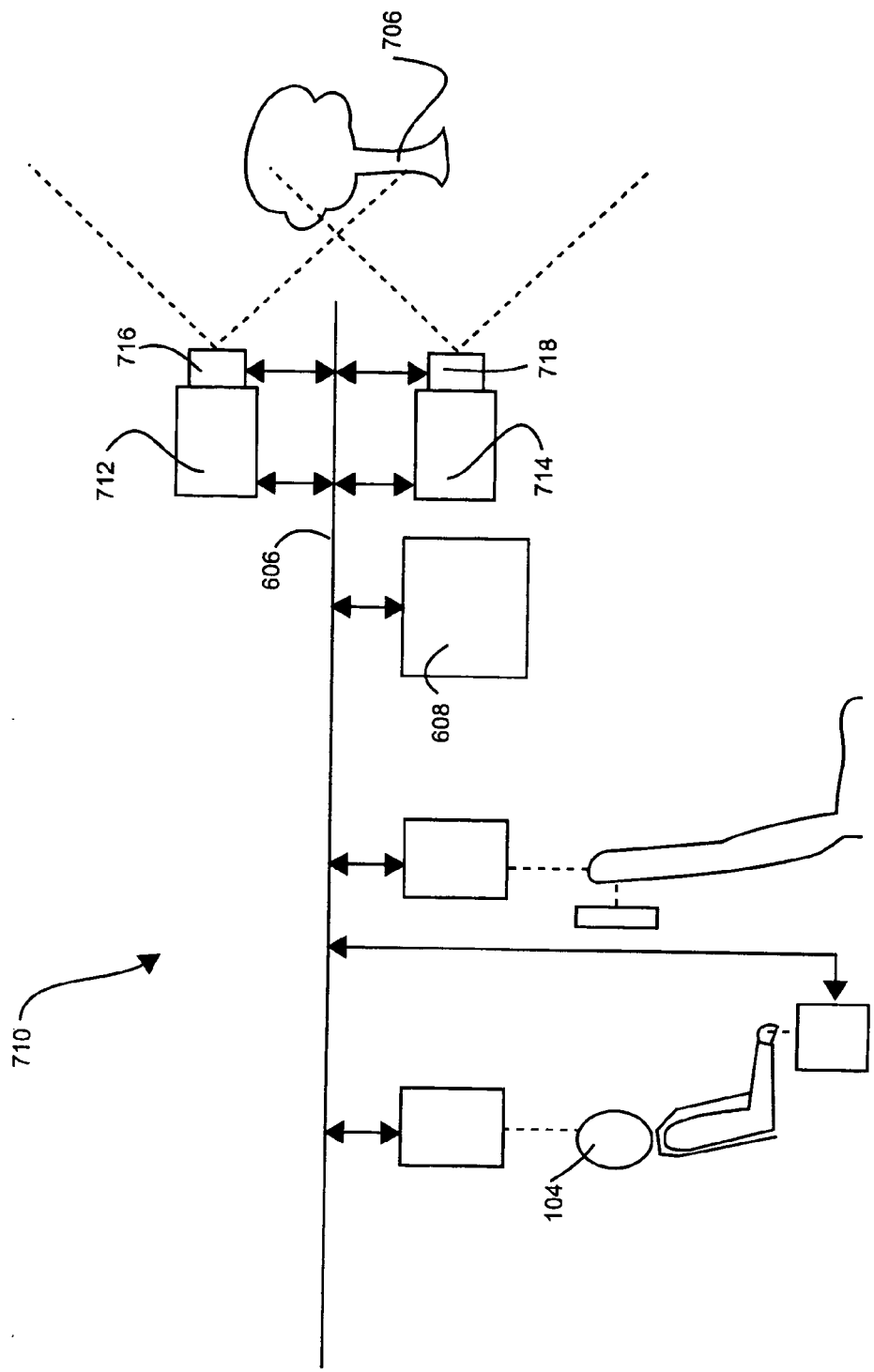
FIG. 12 shows, in block diagram form, a motion sickness reduction device including a stereoscopic camera device according to one embodiment of the invention.

In one embodiment of the invention, as shown in FIG. 12, a motion sickness reduction device 710 includes a communication bus 606 and a processor device 608. The FIG. 12 embodiment also includes a plurality of video cameras, e.g., 712, 714 with respective zoom lens devices 716, 718. In one embodiment of the invention, the video cameras a 712, 714 are adapted to provide stereoscopic image information to processor device 608 and/or occupant 104. According to one embodiment of the invention, the stereoscopic image information includes distance information related to a distance between one or more of the cameras 712, 714 and a feature of the environment such as the illustrated tree 706. In various embodiments, this information is used to adapt the motion sickness reduction device to provide enhanced motion sickness reduction functionality.

Figure 13:
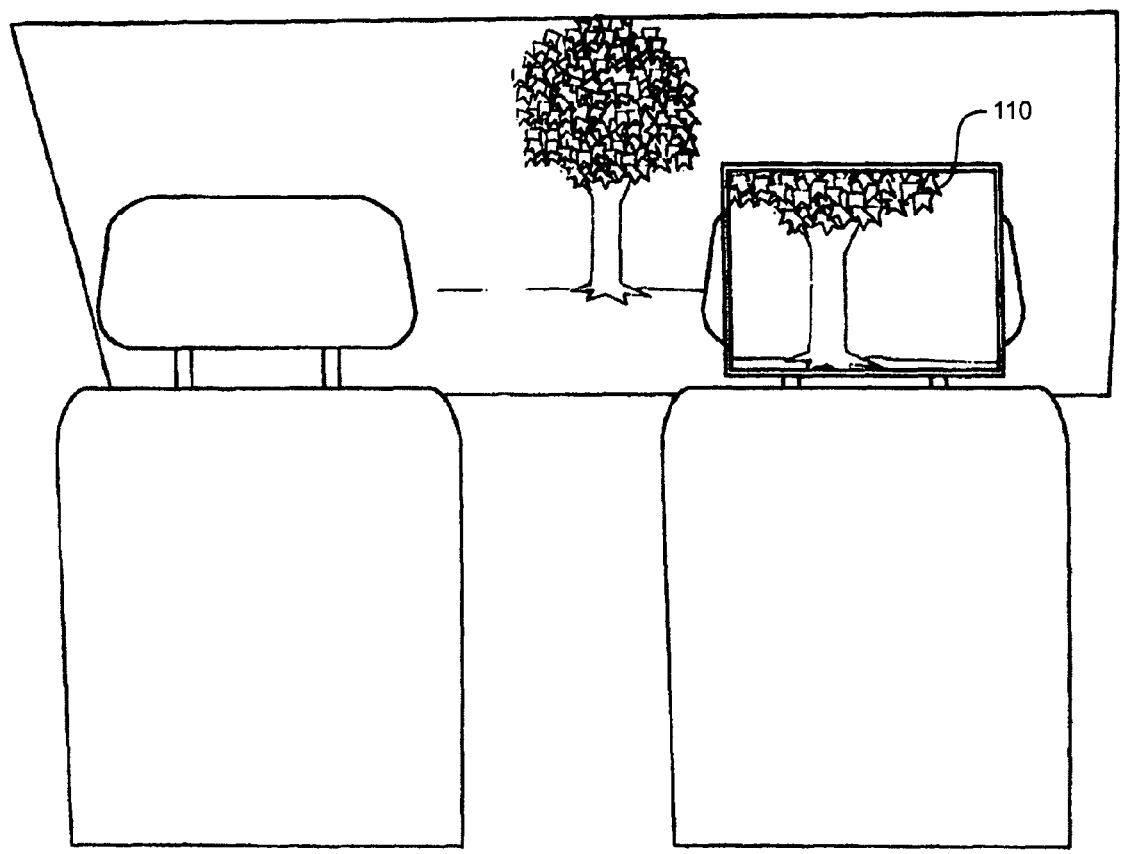
FIG. 13 shows a view outwardly from within a vehicle according to another embodiment of the invention.

FIG. 13 shows a view outwardly from within a vehicle according to another embodiment of the invention. As shown in FIG. 13, according to one embodiment, the video camera e.g., 114, may be located so as to provide an image on the display screen 110 that is different from what would be viewed directly ahead of the occupant 104 (i.e. through the video screen space). For example, the scaling and/or alignment of the image may be different from the corresponding features of an external landmark. Nevertheless, in various embodiments, such an image may be fully effective to provide anti-motion sickness benefits, where the apparent angular velocity of images on the display screen 110 are concordant with those of external images and/or accelerations viscerally sensed by the occupant 104.

Figure 14:
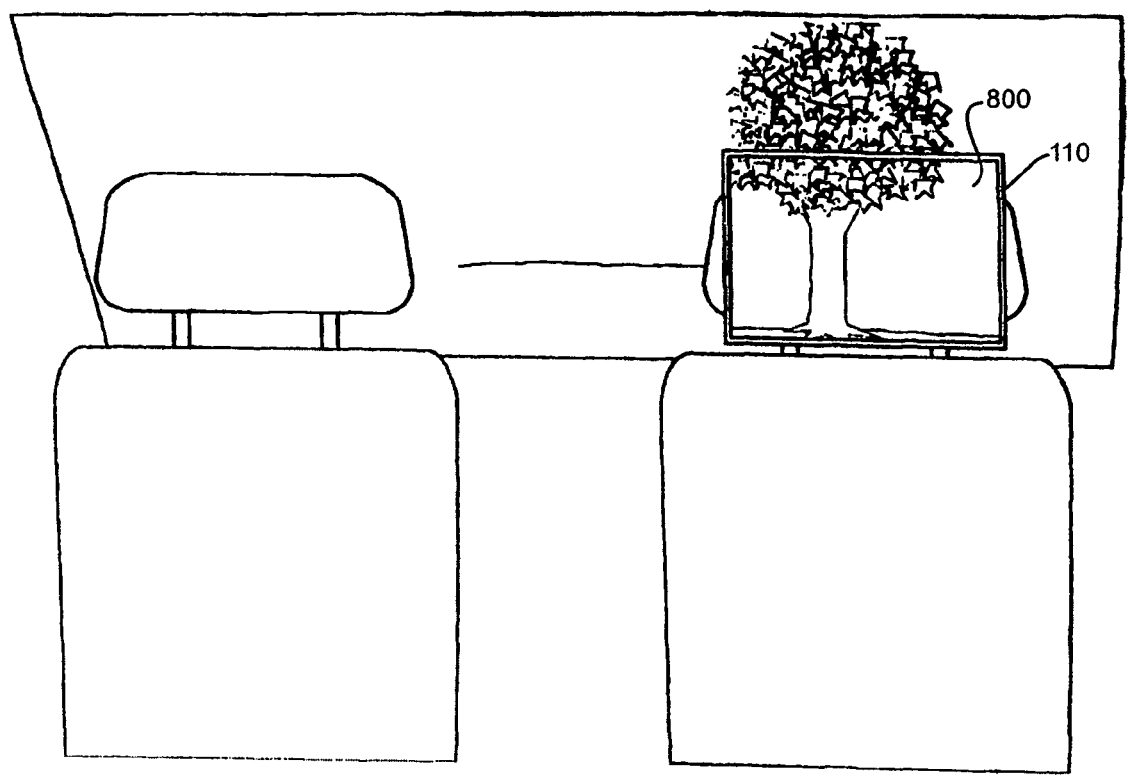
FIG. 14 shows a view outwardly from within a vehicle according to still another embodiment of the invention.

FIG. 14 also shows a view outwardly from within a vehicle according to still another embodiment of the invention. FIG. 14 illustrates that, in one embodiment of the invention, a video camera may be placed to provide an image 800 on a display screen 110 that is substantially aligned with the image that would be viewed by an occupant were the external environment viewed directly through the space of the display screen 110. In one embodiment, this alignment is achieved by placement of a camera in proximity to a head of the occupant. For example, in one embodiment the camera is mounted externally on the vehicle directly above the head of the occupant.

In one embodiment, the camera is mounted on an actuator so as to adjust a position and orientation of the camera according to a detected position of the head of the occupant. Such adjustment of camera position may be made with or without the use of a processor, such as the processor of the FIG. 9 embodiment, to further enhance the motion sickness reducing capabilities of the subject invention.

Figure 15:
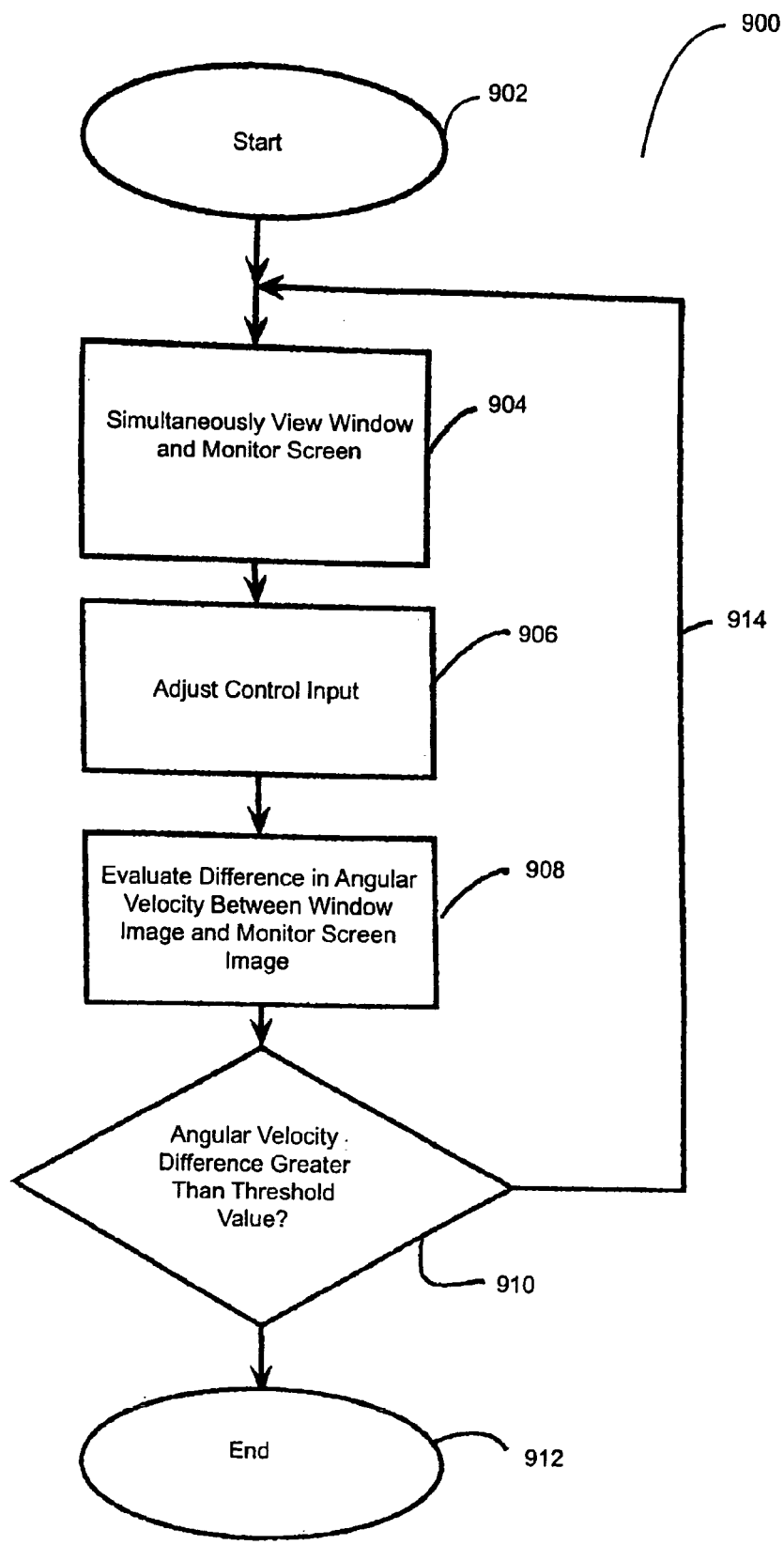
FIG. 15 shows, in flow diagram form, a method of operating a motion sickness reduction device according to one embodiment of the invention.

FIG. 15 shows, in flow diagram form, a method of operating a motion sickness reduction device according to one embodiment of the invention. As shown in FIG. 15, operation of a motion sickness reduction device includes, according to one embodiment, a calibration activity 900. Beginning in an initial state 902 an occupant is within a vehicle such as an automobile. The automobile is placed in motion and the occupant substantially simultaneously views an external apartment through, for example, windscreen and a video monitor showing a dynamic image 904. In response to a perceived differential between, for example, an angular velocity of an image element on the video screen and a corresponding angular velocity of an element of the environment, the occupant adjusts an input to the system 906. As discussed above, in relation to FIG. 9, such adjustment may be made by way of a user interface device available to the occupant. Subsequent to making an adjustment, the occupant reevaluates the respective angular velocities of the video screen image and the external environment 908. If the occupant is satisfied with the correspondence between these angular velocities, the occupant makes a decision 910 to make no further adjustments (at least for the time being) and the calibration activity is completed 912. Otherwise, the occupant may repeat the procedure 914 while making further incremental adjustments.

In various embodiments of the invention, the calibration activity 900 is performed while the vehicle is moved in a turn, over a bump, over an incline, while the vehicle is rotated about a horizontal or vertical axis, a part of the vehicle is raised and/or lowered, or while an external object or image is moved relative to the vehicle. According to one embodiment of the invention, a specialized environment is provided to effect one or more desired calibration motions of the vehicle.

Figure 16:
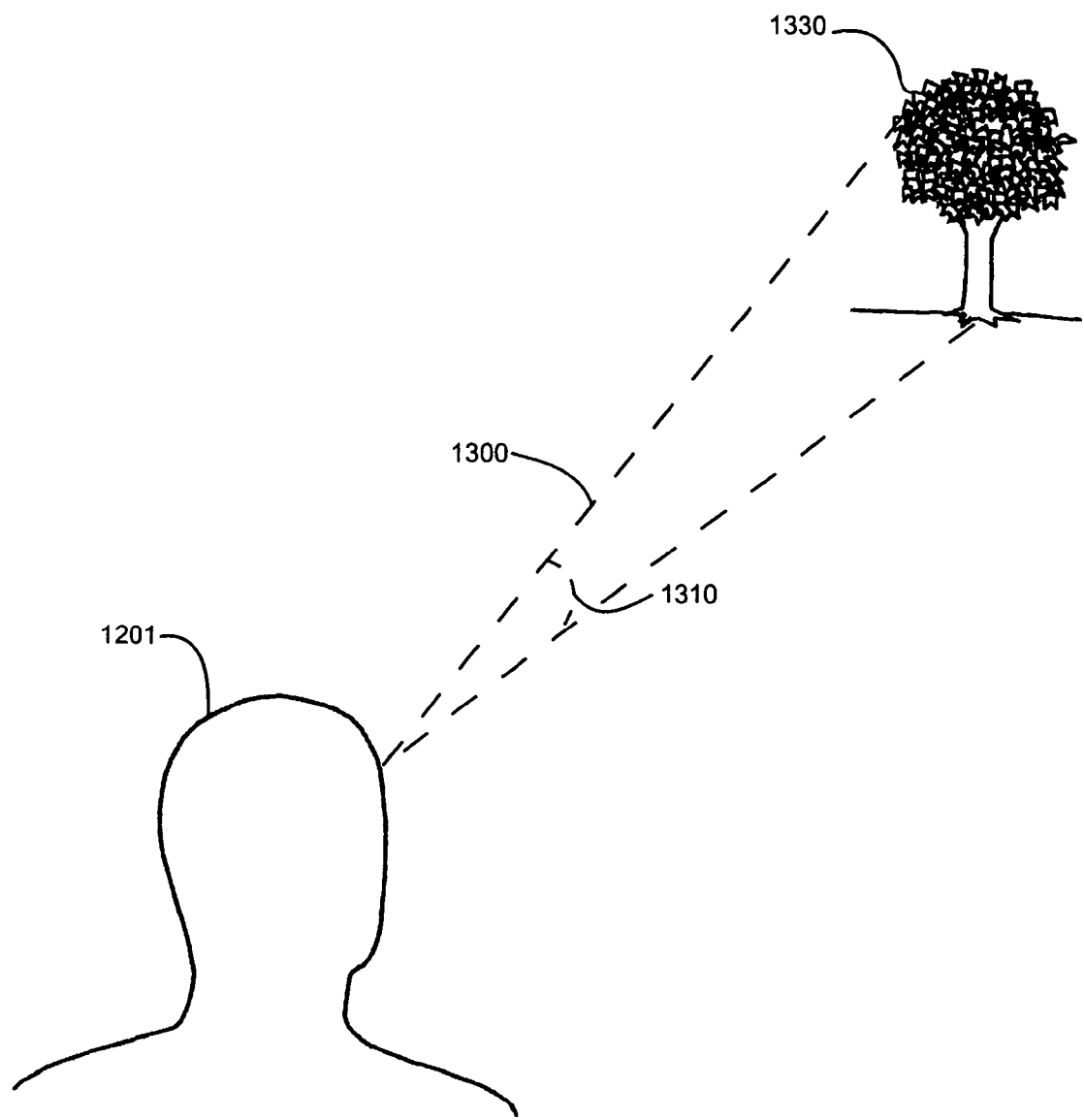
FIG. 16 shows, in schematic perspective view, a viewer and environment according to one aspect of the invention.

In a further embodiment the invention includes a method of adjusting an anti-motion sickness device so that an apparent size of an object in a vehicle's environment is substantially equal to an apparent size of an image of the object displayed within the vehicle. As shown in FIG. 16, a person 1201 views an object 1330 at a distance. A viewing angle of the person 1201 is illustrated by a pair of line segments 1300 shown disposed between the eyes of person 1201 and the top and bottom respectively of object 1330. The pair of line segments 1300 describe an angle 1310.

Figure 17:
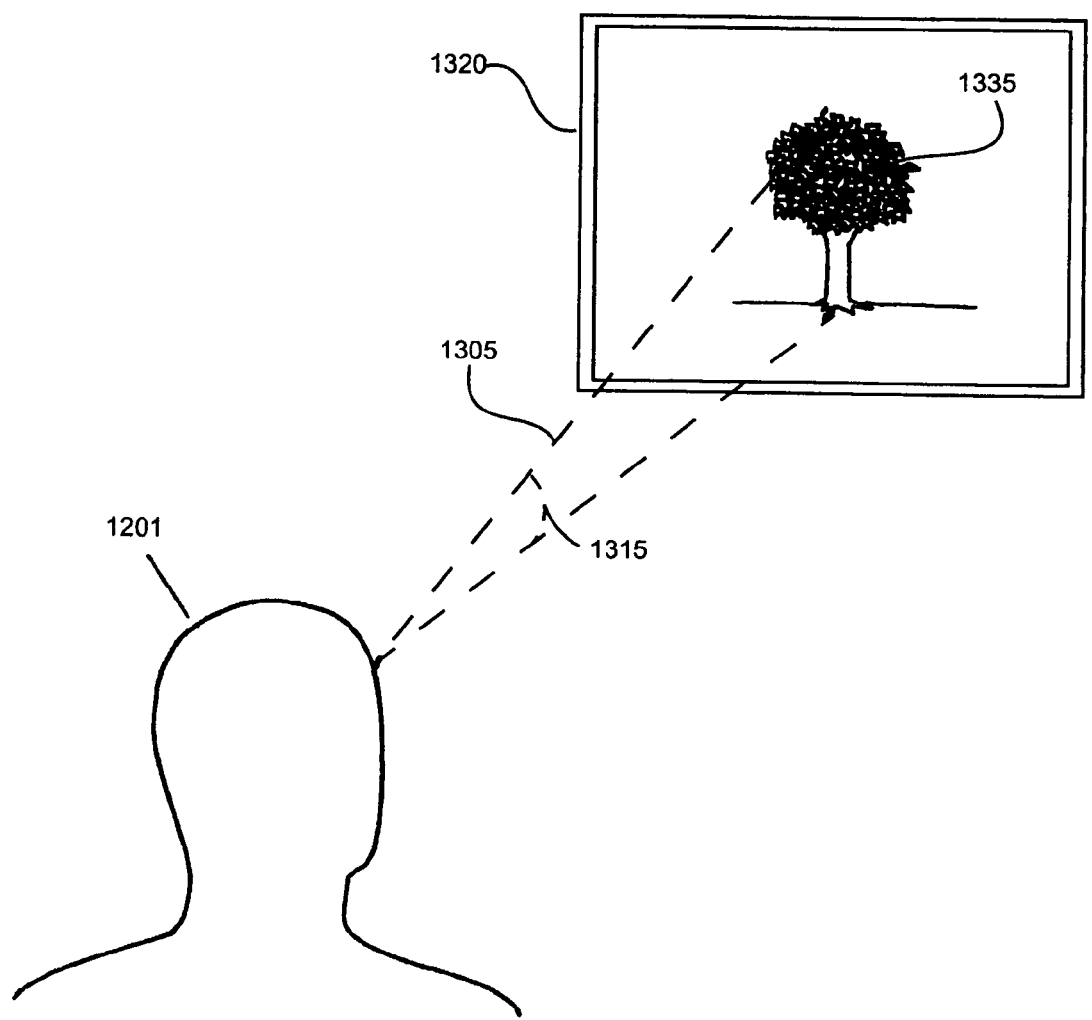
FIG. 17 shows, in schematic perspective view, a viewer and monitor according to one embodiment of the invention.

FIG. 17 shows an image 1335 of the object 1330 of FIG. 16 displayed on a video display screen 1320. A further pair of line segments 1305 are disposed between the eyes of person 1201 top and bottom respectively of image 1335. The further pair of line segments 1305 describe a further angle 1315. When angle 1310 is equal to angle 1315, the apparent size of object 1330 is equal to the apparent size of image 1335.

Figure 18:
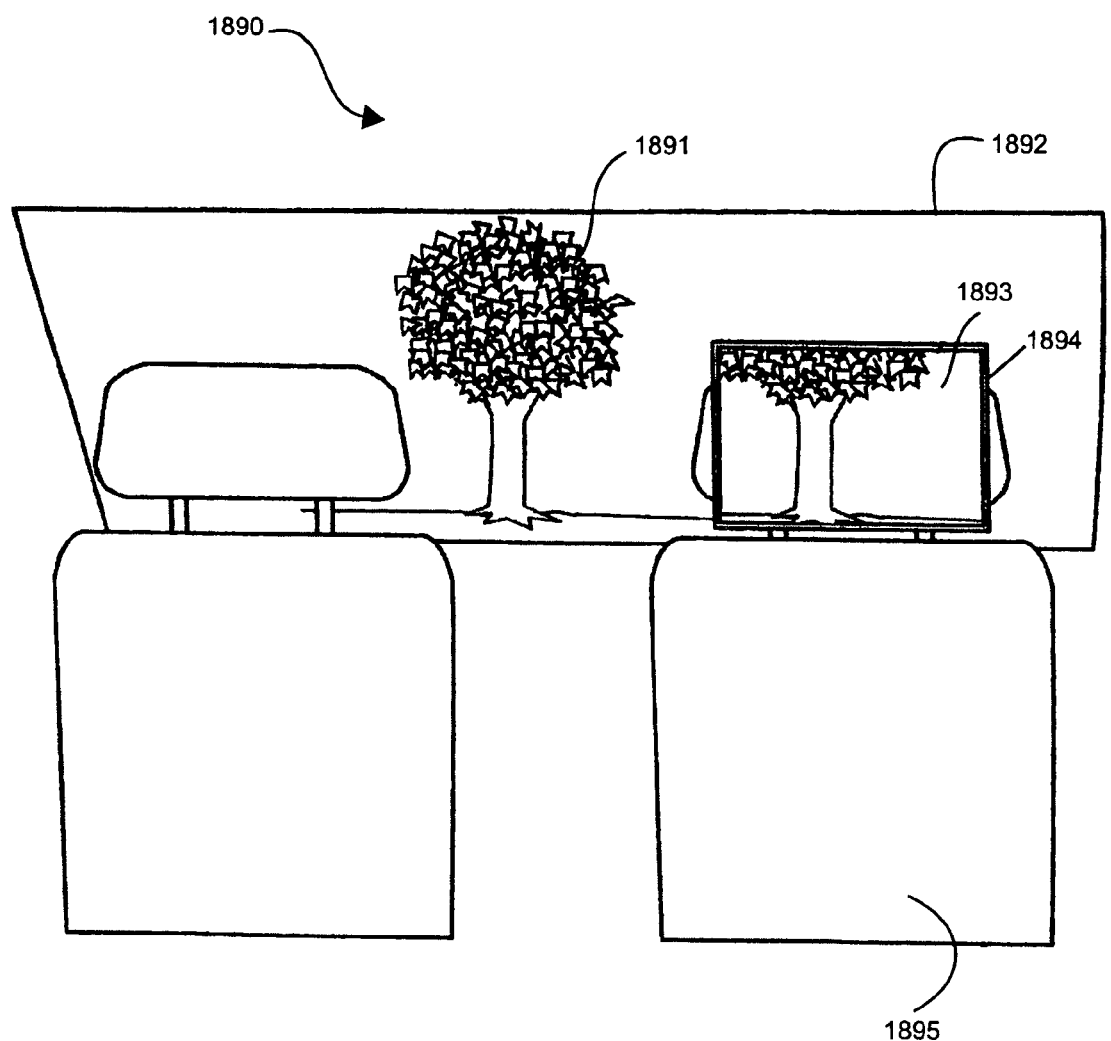
FIG. 18 shows a portion of a vehicle including a monitor according to one embodiment of the invention.

FIG. 18 shows an exemplary view 1890 from a right rear passenger seat of an automobile. The right rear passenger seated is situated directly behind a front passenger seat 1895. A monitor 1894 is supported by a right front passenger seat 1895 and arranged for observation by a viewer in the right rear passenger seat. An external object 1891, illustrated as a tree, is visible beyond a windshield 1892 of the automobile from the right rear passenger seat. An image 1893 of the object 1892 is displayed on the monitor 1894.

From the perspective of a viewer seated in the right rear passenger seat, the scale or size of the image 1893 appears to be the same as that of the object 1891. Under these conditions, a rotation of the automobile relative to the viewer causes the image 1893 to be translated across the monitor 1894 and also causes the object 1891 to be translated across the windshield 1892 such that the respective rates of translation, i.e. the lateral speeds of the image 1893 and object 1891, are substantially equal.

When the rates of lateral translation of the image 1893 and the object 1891 are substantially equal, a likelihood of motion sickness in the viewer is reduced. Therefore, according to one embodiment, the invention includes adjusting the system to equalize an apparent size of the image 1893 and the object 1891. In one embodiment, adjusting the system to equalize an apparent size of image 1893 and object 1891 includes the method of alternately looking at the monitor 1894 and out through the windshield 1892. In another embodiment of the invention, adjusting the system to equalize an apparent size of image 1893 and object 1891 includes a method of simultaneously looking at the monitor 1894 and at the object 1891 through windshield 1892.

In one embodiment, adjusting the system to equalize an apparent size of the image 1893 and the object 1891 includes adjusting a zoom lens of a video camera arranged to capture image 1893 of object 1891. According to one embodiment, adjusting the zoom lens of the video camera includes operating a mechanical coupling such as, for example, a mechanical cable or a mechanical shaft, disposed between a region adjacent to the viewer and the zoom lens. In another embodiment of the invention a adjusting the zoom lens of the video camera includes sending a signal through a signal channel such as, for example, an electrical cable or an optical cable disposed between a region adjacent to the viewer and the zoom lens.

In another embodiment of the invention, adjusting the system to equalize apparent size of the image 1893 and the object 1891 includes adjusting a cropping of the video image. In one embodiment, adjusting a cropping of the video image includes electronic image manipulation of the video image. In another embodiment of the invention, adjusting outcropping of the video image includes adjusting an adjustable mechanical aperture disposed between the monitor 1894 and the viewer.

In yet another embodiment of the invention adjusting the system to equalize an apparent size of the image 1893 and the object 1891 includes adjusting a display size of the image as, for example, by digital image manipulation to expand (stretch) or contract (shrink) the image as displayed on the monitor 1894. According to one embodiment of invention adjustment of the display size includes transmitting a signal to a digital signal processor, the video signal processor including an arithmetic logic unit portion and a memory portion, and using the video signal processor to receive a digitized input video signal and produce a digital output signal adapted to cause the display of a corresponding set of video pixels.

In still another embodiment of the invention adjusting the system to equalize an apparent size of the image 1893 and the object 1891 includes adjusting a position of a video camera with respect to the rear seat of the automobile, and in another embodiment of the invention adjusting the system to equalize an apparent size of the image 1893 and the object 1891 includes adjusting a position of the monitor 1894 with respect to the rear passenger seat of the vehicle. In one embodiment, adjusting a position of the monitor includes activating a motorized mounting bracket of the monitor. In another embodiment, adjusting the position of the monitor includes activating a mechanical linkage between the viewer and a mounting bracket of the monitor.

According to yet another embodiment of the invention, adjusting the system to equalize an apparent size of the image 1893 and the object 1891 includes adjusting a position of the viewer with respect to the monitor 1894. In one embodiment, adjusting a position of the viewer with respect to the monitor 1894 includes adjusting a position of the viewers head, as, for example, by adjusting a headrest disposed in contact with the viewer's head. In another embodiment of the invention, adjusting a position of the viewer with respect to the monitor 1894 includes adjusting a position of the rear passenger seat with respect to the monitor 1894. In various embodiments, adjustment of a passenger seat includes operation of an electronic position adjustment mechanism and operation of a mechanical position adjustment mechanism.

It should be noted that there may be many object visible to the passenger, both as displayed on the monitor 1894 and viewed directly through the windshield 1892. According to various embodiments of the invention the system should be adjusted to approximately equalize the relative size of one or more of the most noticeable objects. According to one embodiment, an adjustment, according to any one of the embodiments described above, should be made and, thereafter, a period of time should be allowed to lapse before a further adjustment is made. According to one embodiment, such a period of time should be on the order of one second. According to another embodiment, such a period of time should be on the order of 10 seconds. According to still other embodiments, the respective periods of time should be on the order of 20 seconds, 30 seconds, 40 seconds, 50 seconds, 60 seconds, two minutes, five minutes, and 10 minutes, for example. In another embodiment of the invention, the passenger continually monitors and adjusts the system to seek the desired relationship between the apparent size of the exterior object and the image on the monitor.

In one embodiment, the invention includes providing instructions to user in relation to operation of the system. According to one embodiment, the user instructions are provided by display of the instructions in video and audio and/or text form on the monitor 1894. According to one embodiment, the user is able to select between various calibration approaches including adjustment of respective apparent sizes and adjustment of respective apparent speed of the image and external object.

Figure 19:
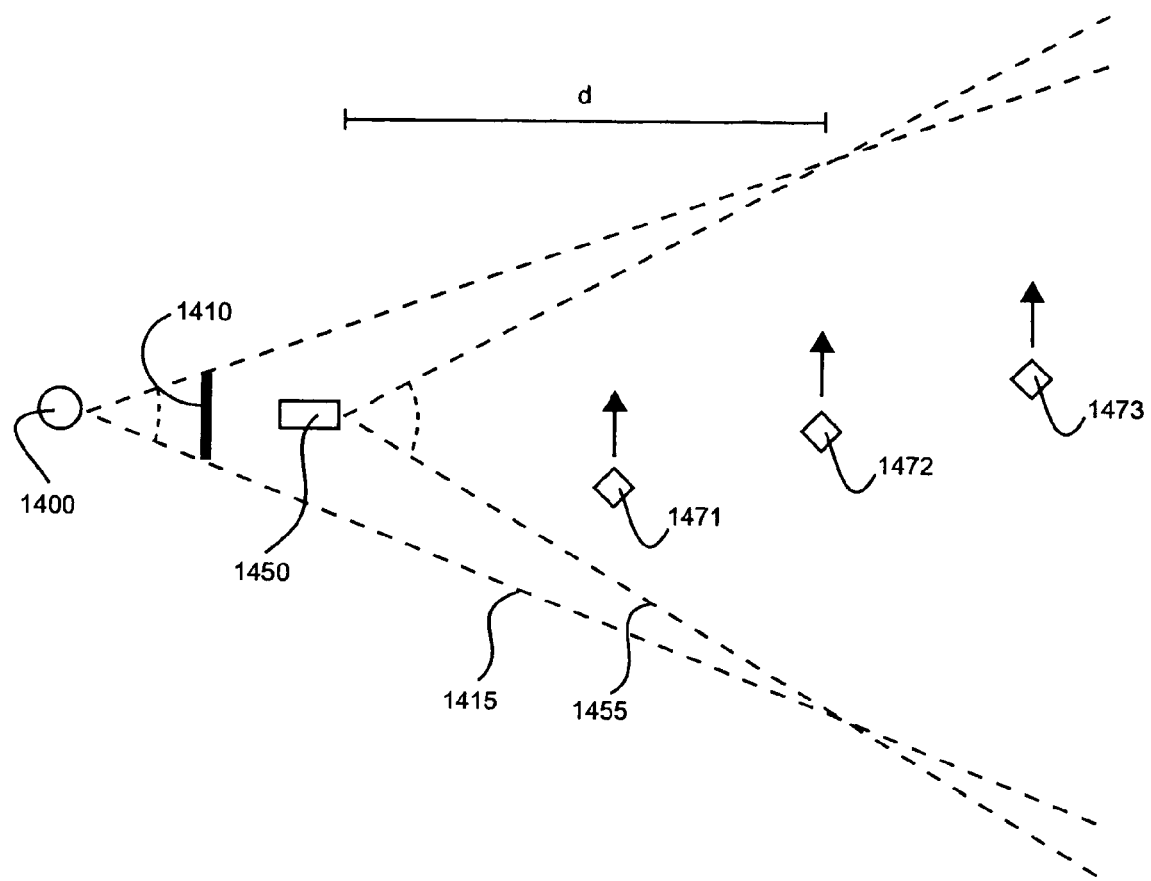
FIG. 19 shows in schematic plan view, a relationship of components according to one embodiment of the invention.

FIG. 19 shows, in schematic plan view, a system according to one embodiment of the invention. In FIG. 19, a person 1400 is viewing an image 1410 which is being fed by a video camera 1450. A first pair of line segments 1455 form a first effective viewing angle at a video camera 1450. A second pair of line segments 1415 form a second effective viewing angle at person 400. The first and second pairs of line segments 1455, 1415 intersect at a distance "d" from the video camera 1450.

Exemplary objects 1471, 1472 and 1473 are in motion and disposed at respective distances from the video camera 1450. Object 1472 is at distance "d" from the video camera 1450. Object 1473 is at a distance greater than "d" from the video camera 1450 and object 1471 is closer to the video camera than distance "d." According to this arrangement, object 1472 will appear in image 1410 to be the same size, and moving at the same speed with respect to person 400 as it would if viewed directly by person 1400. Object 1471 will appear to be larger and moving faster in the image than if it were viewed directly by person 1400.

Figure 20:
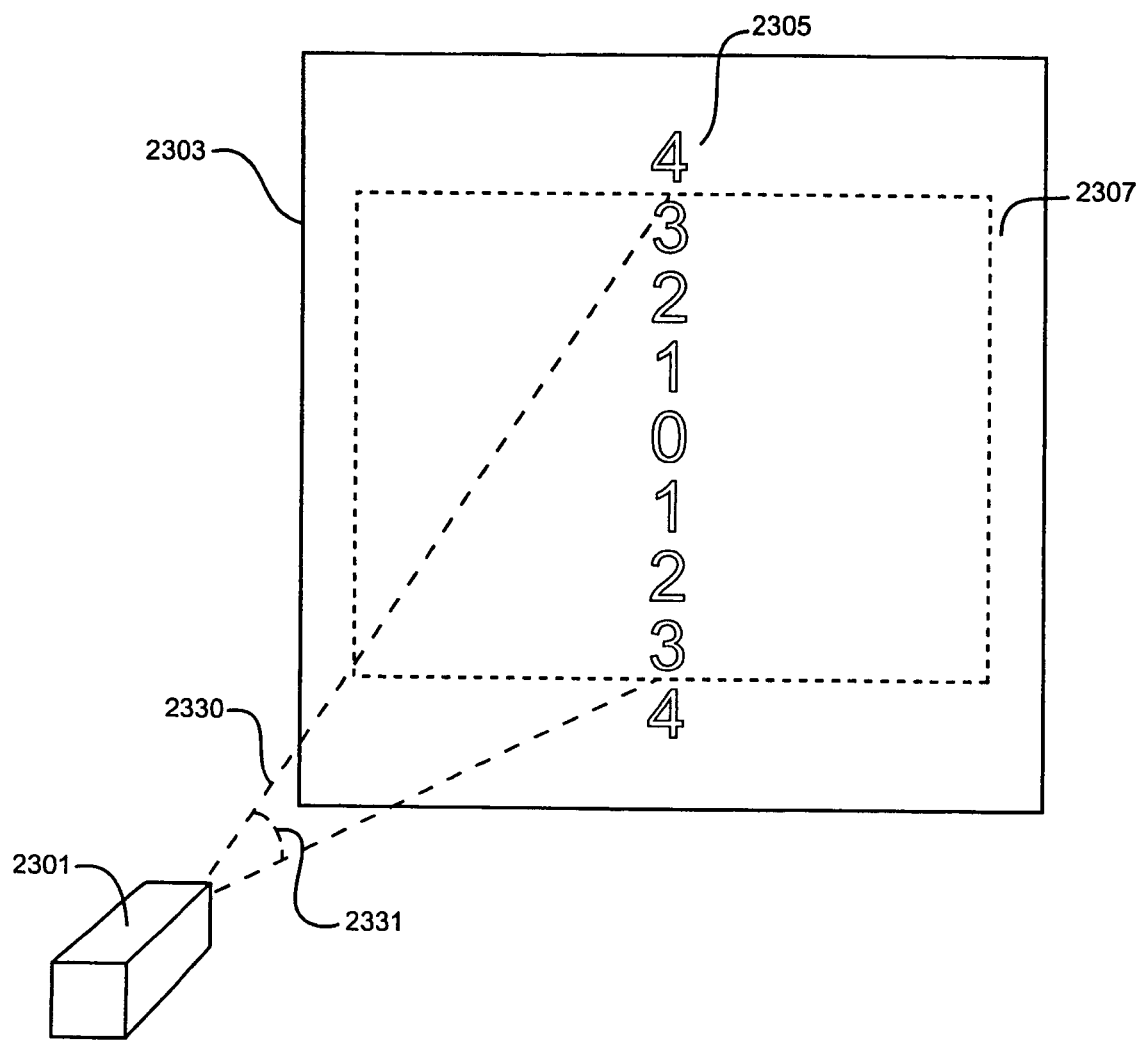
FIG. 20 shows, in schematic perspective view, a video camera and effective viewing angle according to one embodiment of the invention.
Figure 21:
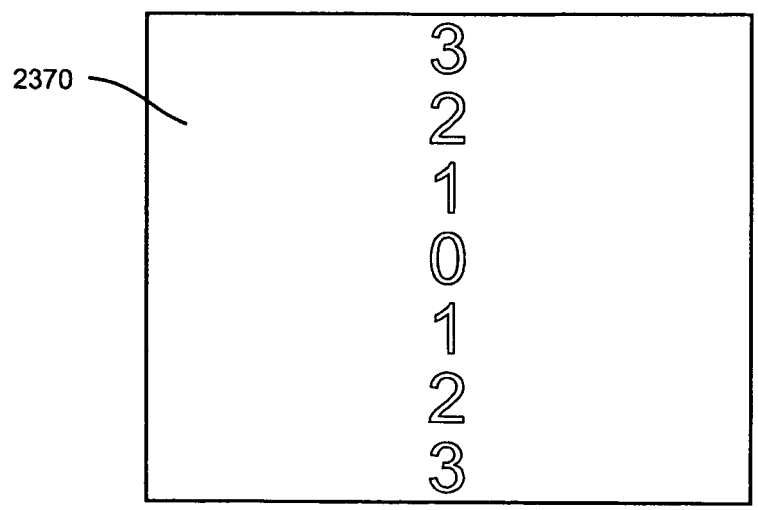
FIG. 21 shows a portion of an image region according to one embodiment of the invention.

In FIG. 20, a video camera 2301 is aimed at a surface 2303, on which is displayed an image 2305, comprising a vertical sequence of numbers.

Figure 31:
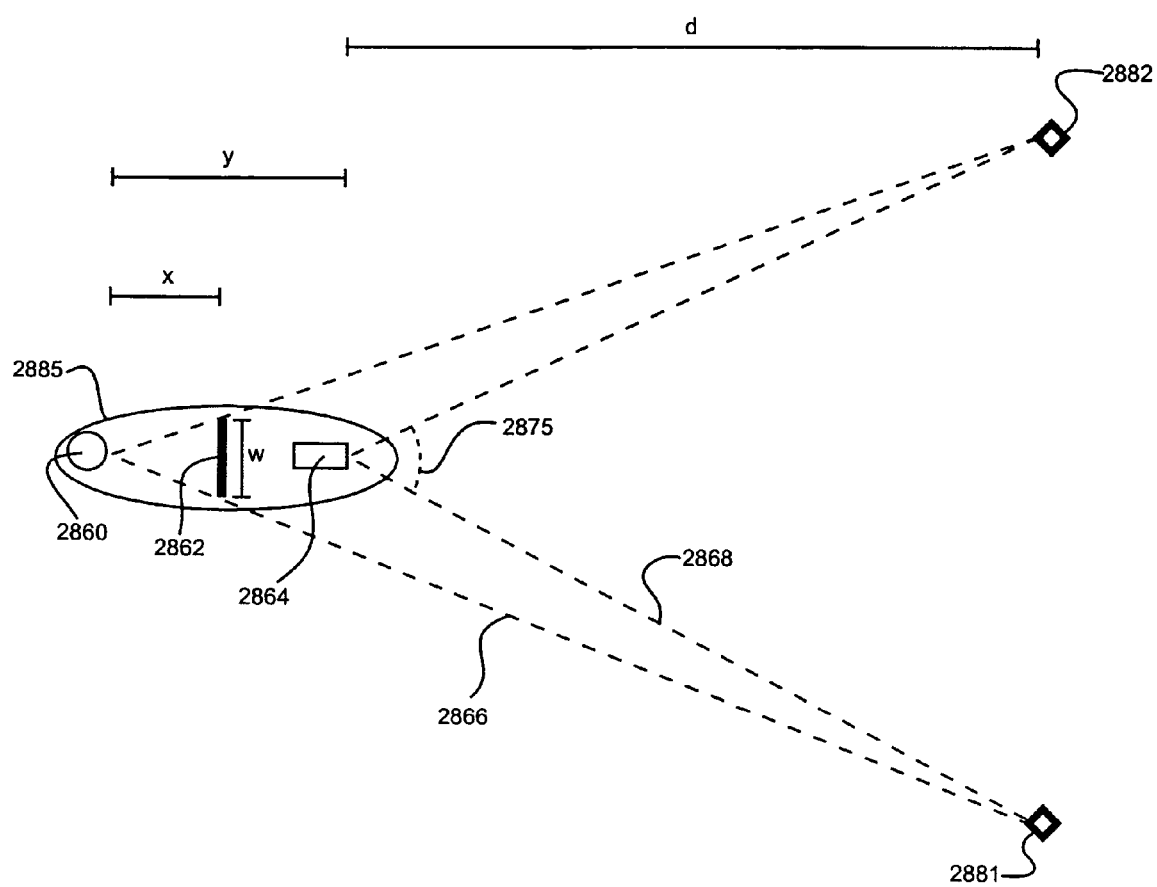
FIG. 31 shows, in schematic plan view, a portion of an antimotion-sickness system and illustrates principles of operation according to one embodiment of the invention.

FIG. 31 shows captured image 2370, representing the image captured by the video camera 2301. In FIG. 20, a box 2307 on surface 2303 illustrates the area captured by the video camera 2301 and represented by image 2370. A pair of line segments 2330 point from the video camera 2301 to the upper and lower ends of the region 2307. A viewing angle 2331 is a measure of the level of zoom of the video camera 2301.

Figure 22:
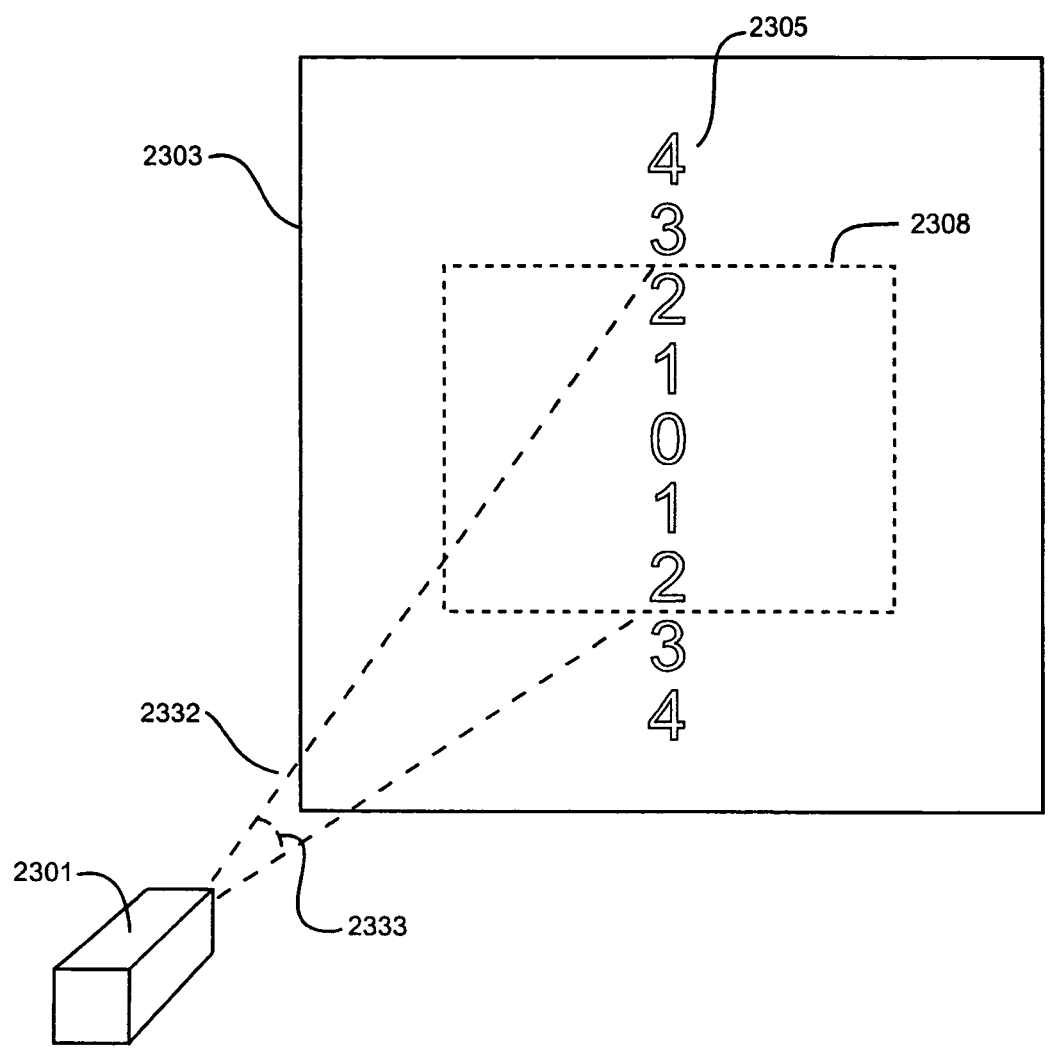
FIG. 22 shows, in schematic perspective view, a video camera and effective viewing angle according to one embodiment of the invention.

FIG. 22 shows video camera 2301 capturing the image of a smaller region 2308 as a result of adjusting the zoom. A viewing angle 2333, formed by line segments 2332, is smaller than the viewing angle 2331 from FIG. 20.

Figure 23:
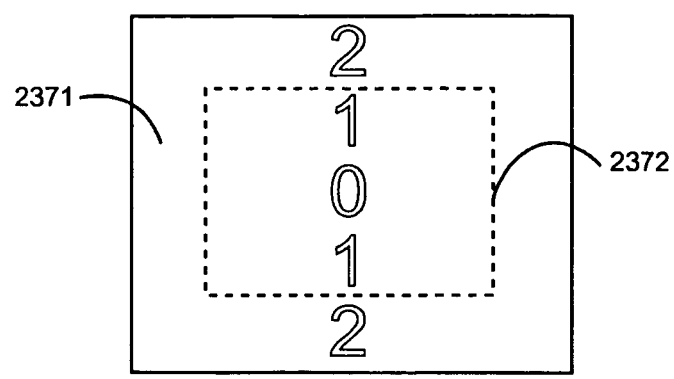
FIG. 23 shows a further portion of an image region according to one embodiment of the invention.

FIG. 23 shows captured image 2371, as a result of the zoom in FIG. 22. This captured image 2371 corresponds with the region 2308 in FIG. 22.

Figure 24:
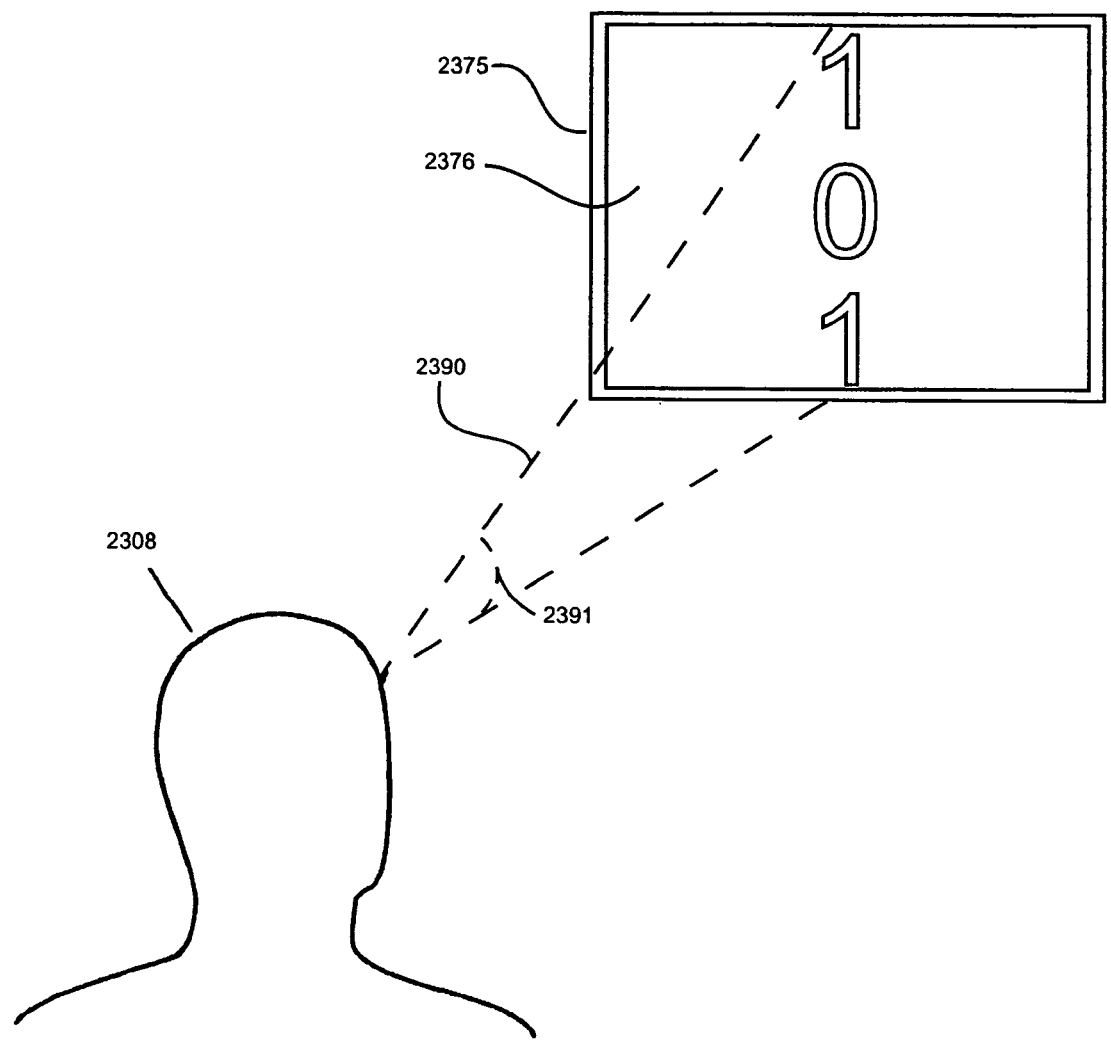
FIG. 24 shows in schematic perspective view, a viewer and monitor according to another embodiment of the invention.

But the entire captured image 2371 may or may not be displayed. In FIG. 24, user 2380 views a monitor 2375, on which is displayed image 2376. Image 2376 corresponds to region 2372 in FIG. 23; region 2372 is a subset of captured image 2371. The display of a subset of the original captured image is called cropping or digital zoom.

In FIG. 24, a pair of line segments 2390 point from the user 2380 to the upper and lower ends of image 2376. Angle 2391, formed by line segments 2390, is the viewing angle of the user 2380.

Figure 25:
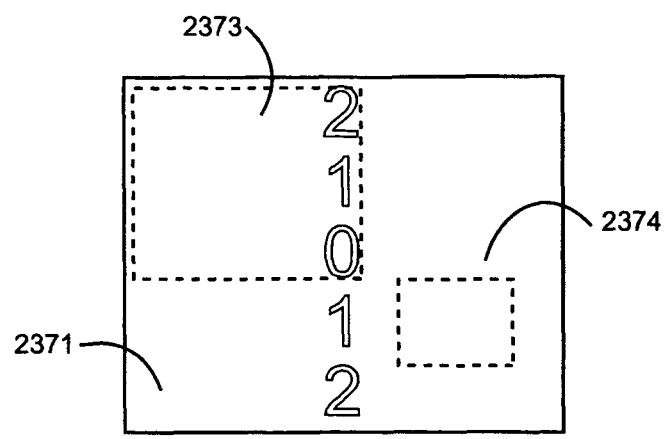
FIG. 25 shows a portion of a monitor display including plural viewing regions according to one embodiment of the invention.

Cropping does not have to be centered on the original image. FIG. 25 shows other ways of cropping an image.

Regions 2373 and 2374 are both non-centered subsets of original captured image 2371, and can be displayed on monitors.

Figure 26:
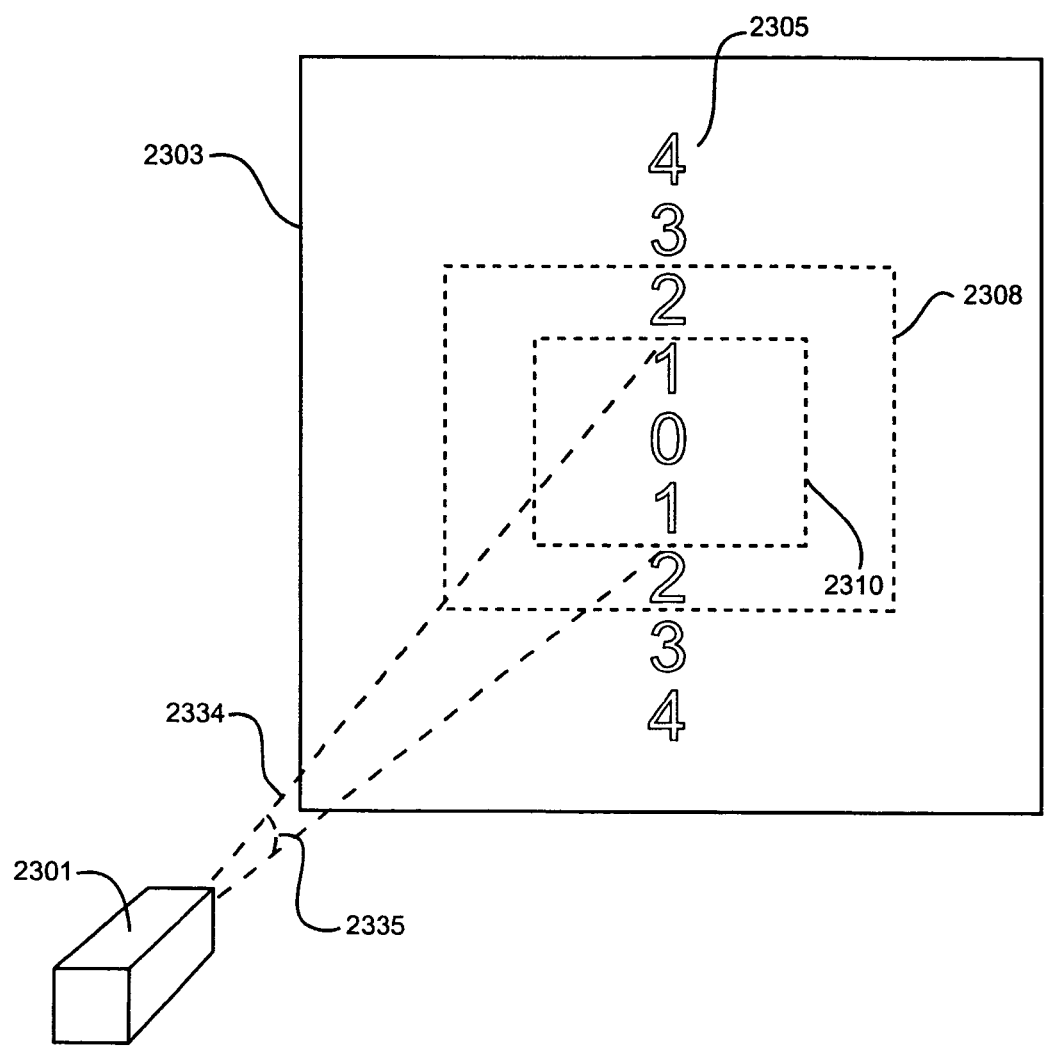
FIG. 26 shows a portion of an anti-motion sickness system including a portion of a monitor display according to one embodiment of the invention.

FIG. 26 illustrates the effective viewing angle 2335 of the camera 2301, based on region 2310, which corresponds to the displayed image 2376 in FIG. 24. A pair of line segments 2334 point from the camera 2301 to region 2310, forming angle 2335, the effective viewing angle of the video camera. Region 2308 corresponds to the actual image captured by camera 2301.

Figure 27:
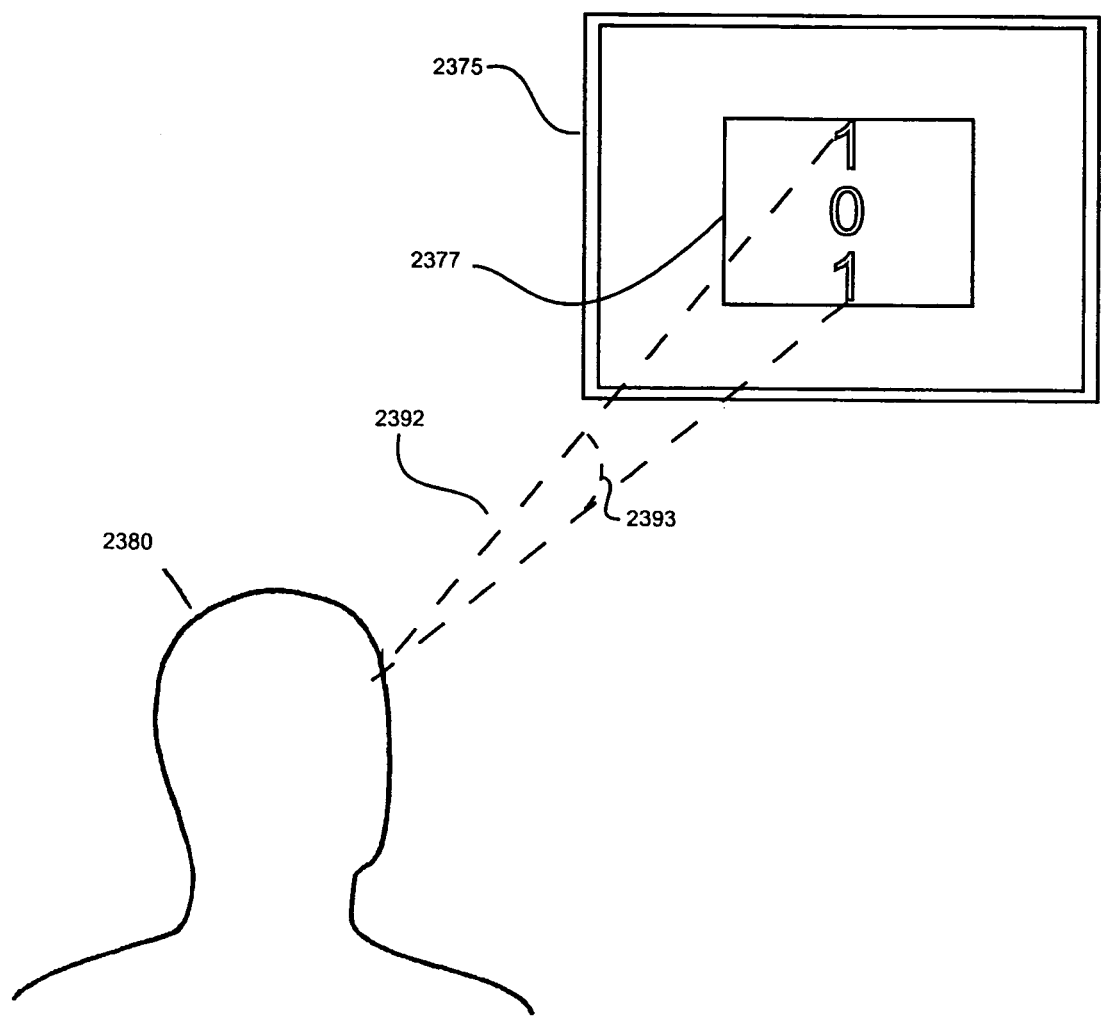
FIG. 27 shows in schematic perspective view, a viewer and monitor according to still another embodiment of the invention.

The video image displayed in a monitor does not have to occupy the entire monitor. In contemporary computer operating systems, images and information is often displayed in a subset of the full monitor, in what are called windows. In FIG. 27, user 2380 views video image 2377, which is displayed in a subset of the display portion of monitor 2375. A pair of line segments 2392, pointing from user 2380 to the top and bottom of video image 2377, form angle 2393, the effective viewing angle of the user.

In one embodiment of this invention, the effective viewing angle of the video camera is set to approximately equal the effective viewing angle of the user. In another embodiment, the effective viewing angle of the video camera is set to be a little greater than the effective viewing angle of the user.

Figure 28:
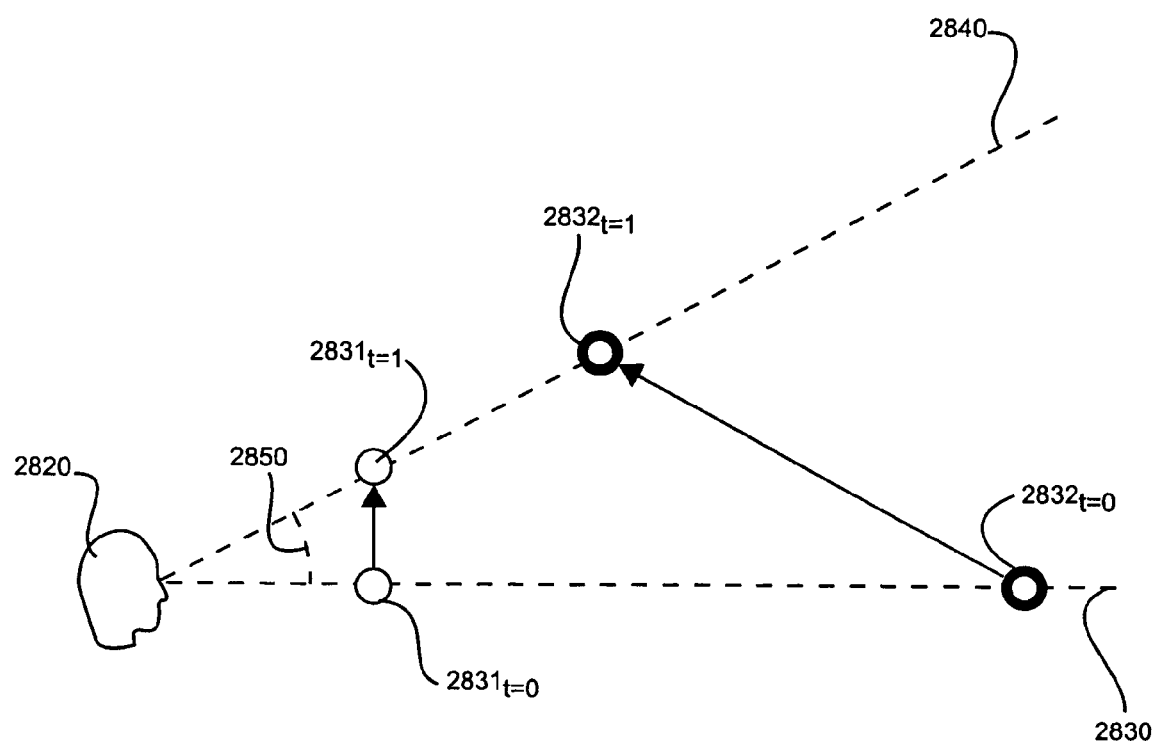
FIG. 28 shows, in schematic elevation, an image relationship according to one amount of the invention.

In FIG. 28, user 2820 views object 2831 and object 2832 along line of sight 2830 at time t=0. Objects 2831 and 2832 move to line of sight 2840 at time t=1. Lines 2830 and 2840 form angle 2850. Because both objects 2831 and 2832 moved the same amount, angle 2850, from the perspective of user 2820, we say that objects 2831 and 2832 have the same apparent angular velocity.

In another embodiment of this invention, the effective viewing angle of the video camera is set so that the apparent angular velocity of an arbitrary object displayed as an image on a monitor matches the apparent angular velocity of an object outside the vehicle.

One method of accomplishing this involves having the passenger simultaneously or alternately look at the monitor and out a window as the vehicle moves relative to the external view and adjusts the system until the apparent angular velocity of the image in the monitor approximately matches the apparent angular velocity of the image viewed through the window.

The apparent angular velocity of the video image depends on many factors, including the zoom of the camera; the position of the camera; the position of the monitor; the cropping of the video image; the size of the displayed image on the monitor; the position of the passenger's head relative to the monitor; the distance, position, and movement of the external objects; and the movement of the vehicle.

Figure 29:
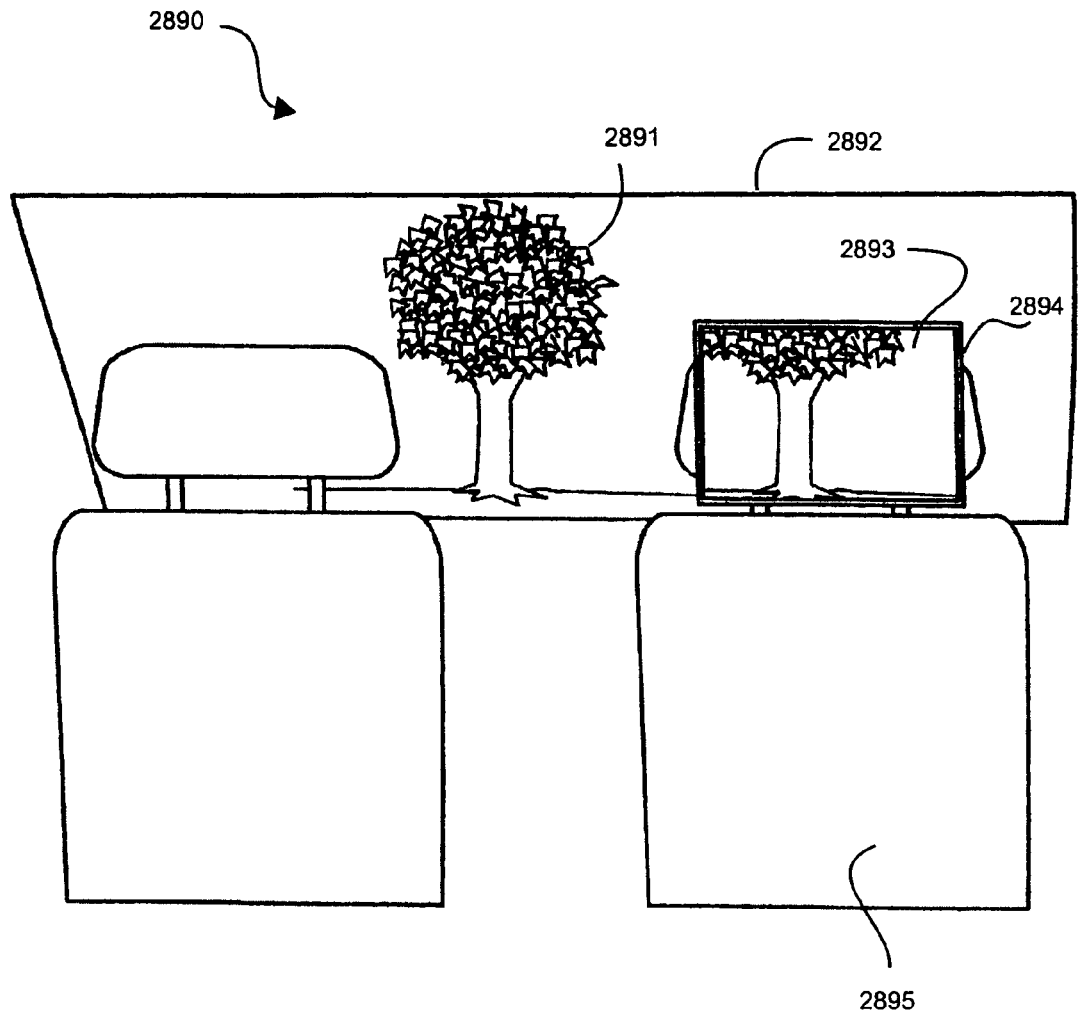
FIG. 29 shows a portion of a vehicle including a monitor according to one embodiment of the invention.

FIG. 29 shows the forward view from the right-rear seat of a passenger vehicle 2890. Directly in front is a monitor 2894, which is attached to the back of a front passenger seat 2895. An external object 2891 appears through a front windshield 2892, and a live video image 2893 is displayed in the monitor 2894.

Note that there may not be a seamless transition of images as viewed through the monitor 894 and out the windshield 2892.

As the vehicle 2890 moves and turns, the external object 2891 will appear to move in the windshield 2892, and the live video image 2893 will appear to move within the monitor 2894. The passenger (not shown) will make adjustments to the system until the images appear to be moving at approximately the same speed.

Moving the vehicle relative to the environment can include moving the vehicle in a turn, moving the vehicle over a bump, a dip, or on an incline, rotating the vehicle about horizontal or vertical axis, raising or lowering part of the vehicle and moving an external object or image relative to the vehicle. Adjusting the system can include adjusting the zoom of camera, adjusting a cropping of a video image, adjusting a size (stretching or shrinking) of the displayed image, adjusting the position of camera, adjusting a position of monitor, adjusting a position of passenger's seat and adjusting a position of a passenger's head.

Figure 30:
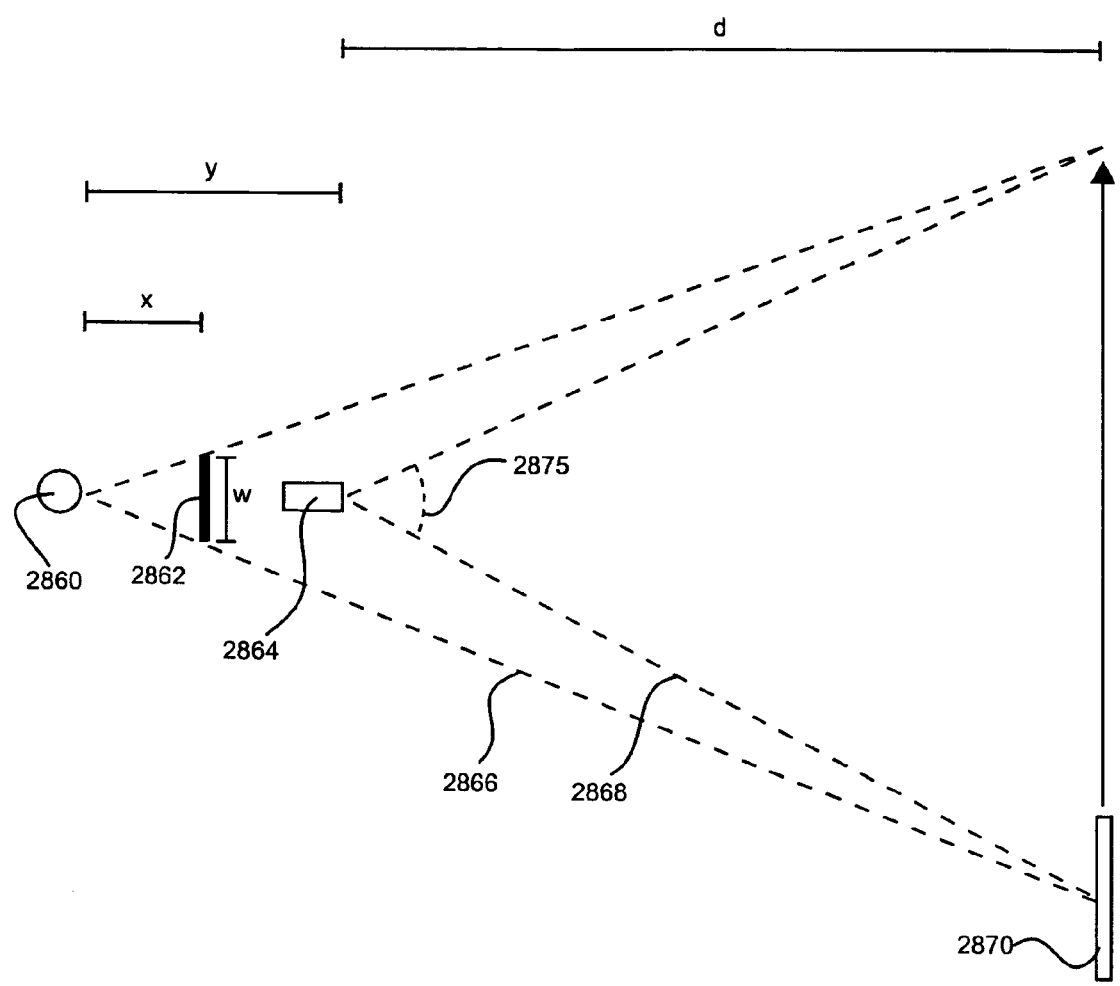
FIG. 30 shows, in schematic plan view, a portion of an antimotion-sickness system according to one embodiment of the invention.

FIG. 30 shows, in schematic plan view, a passenger 2860 viewing a video image 2862 on a monitor (not shown). The width of the image is w. The distance from the passenger 2860 to the video image 2862 is x. A video camera 2864 has an effective viewing angle 2875, formed by line segments 2868. The distance from the passenger 2860 to a point on the video camera 2864 is y.

An object 2870 is a distance d away from the video camera 2864. And the effective viewing angle 2875 of the video camera 2864 is set such that the pair of line segments 2868 intersect the pair of line segments 2866 at a distance d away from video camera 2864. This is the proper setting to ensure that the apparent angular velocity of an object that is a distance d away from the video camera will be the same as the apparent angular velocity of the image in the monitor of that same object.

Object 2870 moves from one end of the video camera 2864's effective visual field (based on the displayed image, not the captured image) to the other. During this same time, the image of object 2870 will move within image 2862 from one end to the other.

In FIG. 31, passenger 2860, video image 2862, and video camera 2864 are in fixed positions in vehicle 2865. Objects 2881 and 2882 are a distance d away from the video camera 2864, and are at opposite sides of the video camera's effective field of view (as defined by the displayed image 2862). The images of objects 2881 and 2882 appear within video image 2862 on opposite sides. The effective viewing angle 2875 of video camera 2864 is set such that line segments 2868 intersect with line segments 2866 at a distance d from video camera 2864.

Figure 32:
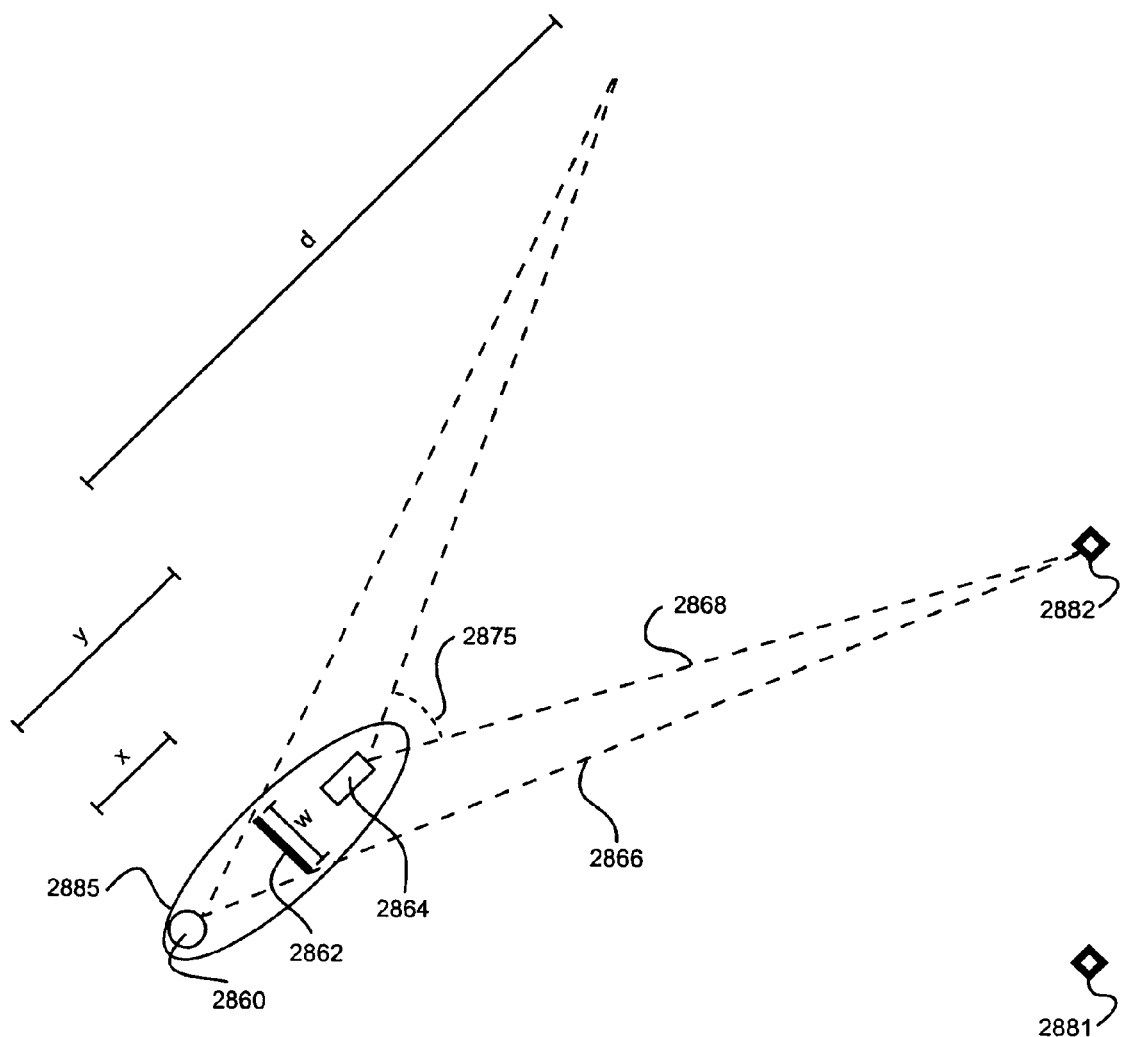
FIG. 32 shows, in schematic plan view, a portion of an antimotion-sickness system and illustrates principles of operation according to one embodiment of the invention.

In FIG. 32, the vehicle 2885 rotates about the passenger such that object 2882 is now at the opposite side of video camera 2864's field of view.

Because the effective viewing angle of the video camera 2864 was set as described above, between FIG. 31 and FIG. 32, the image of object 2882 moved from the left side of the video image 2862 to the right side as the vehicle 2885 rotated, and appeared to the passenger 2860 as a stationary point of reference.

The formula to calculate the effective viewing angle of the camera based on the relative positions of the passenger 2860, the image 2862, the video camera 2864, and the distant object 2882 is:

Effective Viewing Angle of the Video Camera$=2*\arctan(w(y+d)/(2*x*d))$

Figure 33:
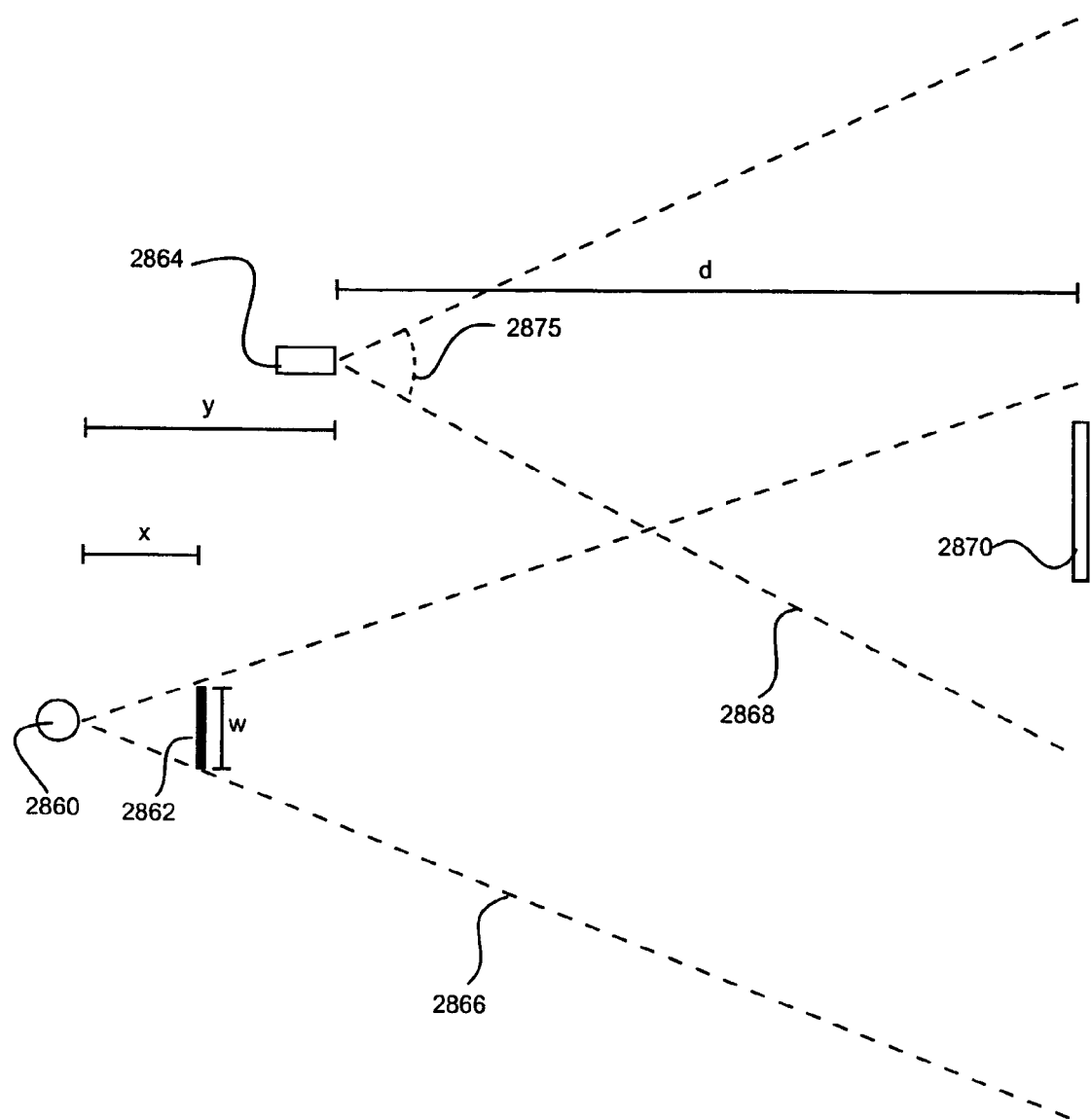
FIG. 33 shows, in schematic plan view, a portion of an antimotion-sickness system and illustrates principles of operation according to another embodiment of the invention.

The video camera does not have to be directly in line with the passenger and the displayed video image in order to effectively prevent motion sickness. In FIG. 33, video camera 2864 is positioned to one side. The effective viewing angle 2875 is determined the same as before, based on the relative positions of the passenger, video image, video camera, and distant object.

Figure 34:
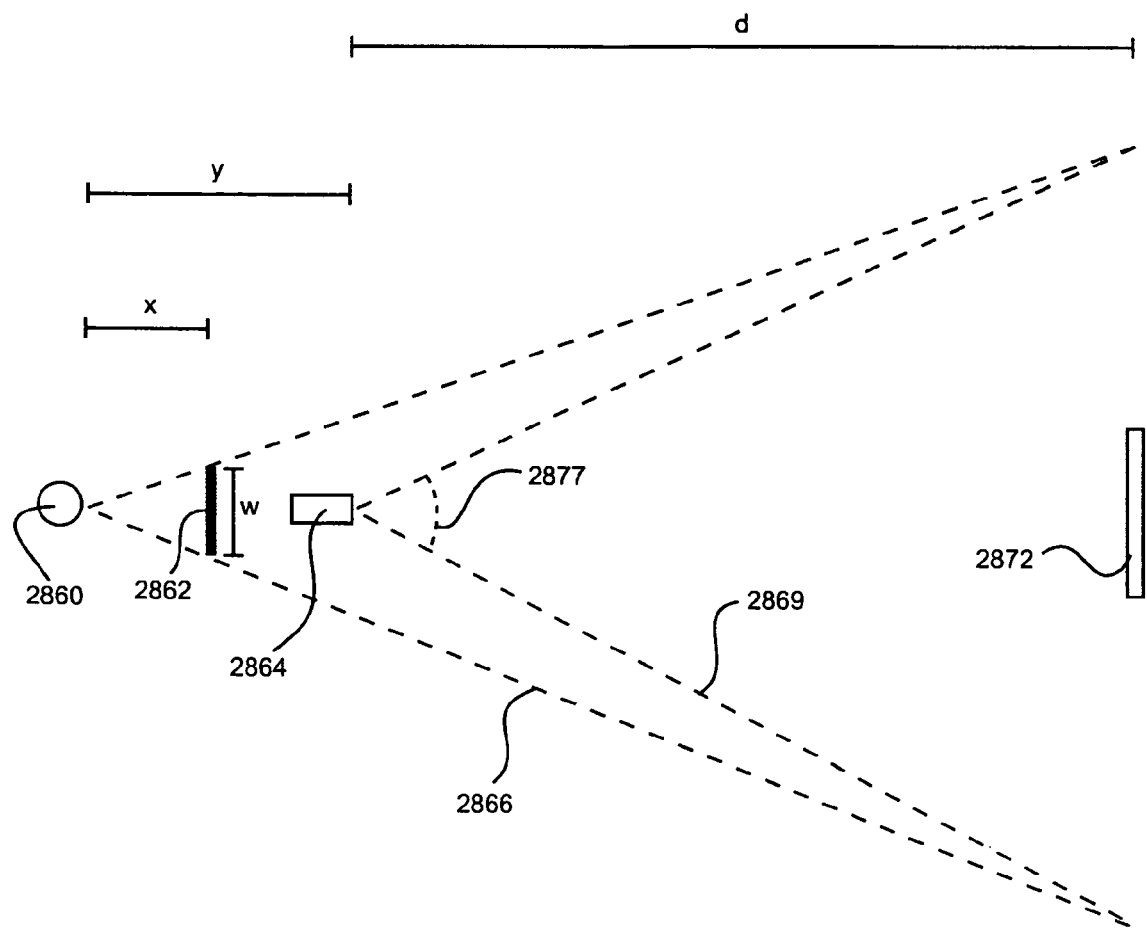
FIG. 34 shows, in schematic plan view, a portion of an antimotion-sickness system and illustrates principles of operation according to still another embodiment of the invention.

In FIG. 34, object 2872 is closer to the video camera 2864 than before. And so the distance d from the video camera 2864 to the object 2872 is smaller relative to x and y. This results in a larger effective viewing angle 2877 of video camera 2864.

Figure 35:
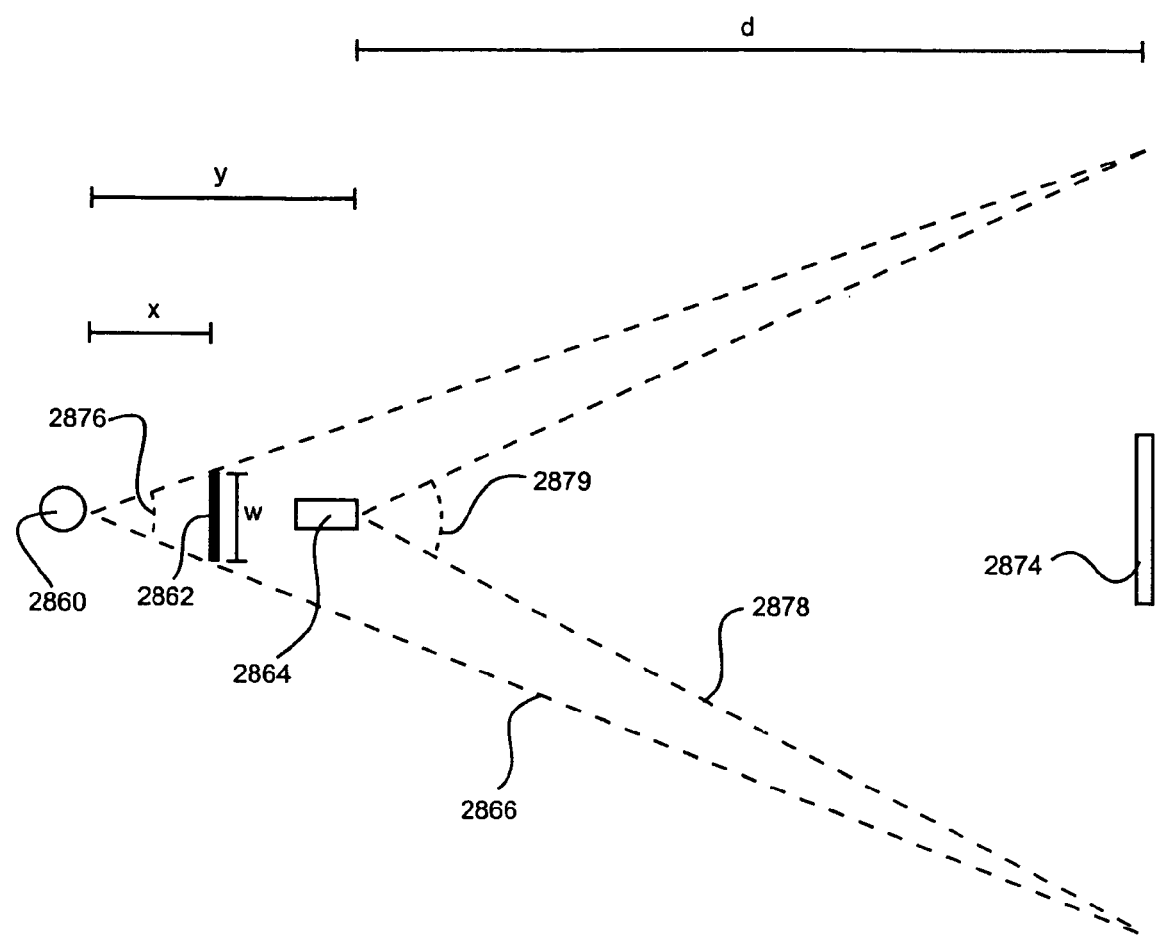
FIG. 35 shows, in schematic plan view, a portion of an antimotion-sickness system and illustrates principles of operation according to yet another embodiment of the invention.

In FIG. 35, object 2874 is farther away than it was in FIG. 30, and the distance d becomes larger relative to x and y. This results in a smaller effective viewing angle 2879 of video camera 2864. As a general principle, as the object moves farther away, the effective viewing angle becomes closer to the effective viewing angle 2876 of passenger 2860. At a sufficiently far distance, the two angles become close enough that setting the effective viewing angle of the video camera 2864 to equal the effective viewing angle of passenger 2860 will prevent motion sickness.

In another embodiment, the invention automatically adjusts the effective viewing angle of the video camera based on the distance to arbitrary distant objects and the physical configuration of the system and passenger. The system comprises a distance detector, which measures the distance to an object in view of the video camera.

In one embodiment, the system measures the distance to an object in a single fixed direction relative to the vehicle.

In another embodiment, one or more range finders measure distances with different aims, and the system selects the distance measurement based on the motion of the vehicle, the motion of distant objects, and/or the size of distant objects.

In another embodiment, the selection of measured distance is based on the analysis of an image.

In another embodiment, when the effective viewing angle of the passenger increases or decreases, the system automatically increases or decreases, respectively and approximately proportionally, the effective viewing angle of the video camera.

The effective viewing angle of the passenger increases when the monitor moves towards the passenger's head. The effective viewing angle of the passenger also increases when the monitor may be mounted to the seat in front of the viewing passenger, and so the position of the seat, or seat-back, in front of the viewing passenger can be used as a proxy for the position of the monitor and when the passenger's head moves towards the monitor.

The system can use the position of the passenger's seat as a proxy for the position of the passenger's head. The system can also use a sensor to directly determine the movement of the passenger's head. Responsively, the size of the image of the monitor can be increased or decreased.

In some embodiments, the video image is displayed on a subset of the monitor screen. When the effective viewing angle of the passenger increases, the system will automatically increase the effective viewing angle of the video camera approximately the same amount. This can be done by one or a combination of adjusting the zoom of the video camera to increase the video camera's field of view and adjusting the cropping of the video image to display a greater portion of the original captured video image.

The effective viewing angle of the passenger decreases when the monitor moves away from the passenger's head, when the passenger's head moves away from the monitor and/or when the size of the image on the monitor decreases.

When the effective viewing angle of the passenger decreases, the system will automatically decrease the effective viewing angle of the video camera approximately the same amount. This can be done by one or a combination of adjusting the zoom of the video camera to decrease the video camera's field of view and adjusting the cropping of the video image to display a smaller portion of the original captured video image.

In the case where the monitor's position changes, the system, according one embodiment, automatically adjusts a cropping and/or a stretching/shrinking of the video image and/or a zoom degree of the video camera. In one embodiment, a single switch controls the position of the forward seat and monitor, and may simultaneously control the effective viewing angle of the video camera.

The position of the forward seat and monitor is changed manually or via a switch connected to a motor, and the position or movement of the seat or monitor is detected by the system, which adjusts the effective viewing angle of the video camera.

The system determines the position of the seat and monitor on demand, intermittently, or continually, and adjusts the effective viewing angle of the video camera.

In another embodiment, the system automatically maintains a constant effective viewing angle of the passenger. When the passenger's head moves toward the monitor, or the monitor moves toward the passenger's head, the system automatically reduces the size of the displayed video image to keep the effective viewing angle of the passenger the same as before. When the passenger's head moves away from the monitor, or the monitor moves away from the passenger, the system automatically increases the size of the displayed video image to keep the effective viewing angle of the passenger the same as before.

In another embodiment, this invention detects the speed of the vehicle and adjusts the system at least partly depending on that speed. In another embodiment, this invention detects the degree of turn of the vehicle and adjusts the system at least partly depending on that degree of turn. The system may detect the degree of turn based on the position of the orientation of one or more of the wheels of the vehicle, or of the steering wheel, using one or more sensors.

In another embodiment, this invention displays the captured image or a subset of the captured image such that the ratio of its width and height does not match the ratio of the width and height of the captured image. Vertical motion in the image is generally caused by the vehicle's pitching, and horizontal motion in the image is generally caused by the vehicle's yawing. Because the radius of turn in a pitch may be much different from the radius of turn in a yaw, the relative speeds of vertical and horizontal motion in the image may need to be adjusted by changing the proportion of height and width in the live video image.

While the exemplary embodiments described above have been chosen primarily from the field of automotive transportation, one of skill in the art will appreciate that the principles of the invention are equally well applied, and that the benefits of the present invention are equally well realized in a wide variety of other moving environment systems including, for example, aeronautical systems. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A method for adjusting a motion sickness reduction device comprising: observing from a vehicle an apparent size of an external object outside said vehicle and an apparent size of an image of said object on a display device within said vehicle from a perspective of a viewer;

adjusting said image of said object on said display device to substantially equalize said apparent size of said external object and said apparent size of said image of said object into a relationship such that said viewer would perceive substantially the same image if visible directly or via said display screen; and periodically further adjusting said image size of said object on said display device to maintain said relationship.

2. A method for adjusting a motion sickness device as defined in claim 1 wherein said adjusting said image of said object comprises adjusting a zoom lens of a video camera, said video camera being adapted to produce an image signal corresponding to said image of said object.

3. A method for adjusting a motion sickness device as defined in claim 1 wherein said adjusting said image of said object comprises cropping said image of said object.

4. A method for adjusting a motion sickness device as defined in claim 1 wherein said adjusting said image of said object comprises stretching said image of said object.

5. A method for adjusting a motion sickness device as defined in claim 1 wherein said adjusting said image of said object comprises shrinking said image of said object.

6. A method for adjusting a motion sickness device as defined in claim 1 wherein said adjusting said image of said object comprises manually adjusting an image display device.

7. A method for adjusting a motion sickness device as defined in claim 1 wherein said adjusting said image comprises adjusting a distance between a viewer and a display screen, said display screen being adapted to display said image of said object.

8. A method for adjusting a motion sickness device as defined in claim 7 wherein said adjusting a distance between said viewer and said display screen comprises moving a vehicle seat, said vehicle seat being adapted to support said viewer.

9. A method of adjusting a motion sickness reduction system comprising:

providing an image signal from a video camera to a display screen, said video camera having an effective viewing angle, positioning a display screen of said system in spatial relation to a user of said display screen and in spatial relation an external landmark according to the formula: Effective Viewing Angle of the Video Camera=$2*\arctan(w*(y+d)/(2*x*d))$, wherein d represents a distance between said video camera and said external landmark, y represents a distance between said video camera and said user, x represents a distance between said display screen and said user, and w represents a dimension of said display screen.

10. A method of adjusting a motion sickness reduction system as defined in claim 9 further comprising evaluating said formula by reference to a lookup table.

11. A method of adjusting a motion sickness reduction system as defined in claim 9 where said positioning said display screen of said system in relation to said user comprises automatically sensing distance d using a rangefinder.

12. A method of adjusting a motion sickness reduction system as defined in claim 9 where said positioning said display screen of said system in relation to said user comprises automatically adjusting the Effective Viewing Angle by adjusting a zoom lens of said video camera.

13. A method of adjusting a motion sickness reduction system as defined in claim 9 where said positioning said display screen of said system in relation to said user comprises receiving a rangefinder input at a processor device and solving said formula.

\* \* \* \* \*